US011844679B2

(12) United States Patent
Sachar et al.

(10) Patent No.: US 11,844,679 B2
(45) Date of Patent: Dec. 19, 2023

(54) INTERVENTIONAL DEVICE HAVING AN INTEGRATED EMBOLIC FILTER AND ASSOCIATED METHODS

(71) Applicant: CONTEGO MEDICAL, INC., Raleigh, NC (US)

(72) Inventors: Ravish Sachar, Raleigh, NC (US); Udayan Patel, San Jose, CA (US)

(73) Assignee: Contego Medical, LLC, Raleigh, NC (US)

( * ) Notice: Subject to any disclaimer, the term of this patent is extended or adjusted under 35 U.S.C. 154(b) by 147 days.

(21) Appl. No.: 17/512,920

(22) Filed: Oct. 28, 2021

(65) Prior Publication Data

US 2022/0142765 A1    May 12, 2022

Related U.S. Application Data

(63) Continuation of application No. 16/380,445, filed on Apr. 10, 2019, now Pat. No. 11,166,802, which is a (Continued)

(51) Int. Cl.
*A61F 2/01*    (2006.01)
(52) U.S. Cl.
CPC .......... *A61F 2/01* (2013.01); *A61F 2002/016* (2013.01); *A61F 2230/005* (2013.01); *A61F 2230/0067* (2013.01); *A61F 2230/0078* (2013.01)
(58) Field of Classification Search
CPC ...... A61F 2/01; A61F 2/013; A61F 2002/015; A61F 2002/016; A61F 2230/005; A61F 2230/0067; A61F 2230/0078
See application file for complete search history.

(56) References Cited

U.S. PATENT DOCUMENTS 4,723,549 A    2/1988 Wholey et al.
5,053,008 A    10/1991 Bajaj
(Continued)

FOREIGN PATENT DOCUMENTS

CA      2683468 A1    4/2010
JP   2002336261 A    11/2002
(Continued)

OTHER PUBLICATIONS

Second Office Action for Canadian Application No. 2,974,532 dated Sep. 1, 2022, 4 pages.
(Continued)

*Primary Examiner* — Tuan V Nguyen
(74) *Attorney, Agent, or Firm* — Meunier Carlin & Curfman LLC

(57) ABSTRACT

A percutaneous transluminal angioplasty device, comprising an elongated catheter, an interventional device operably coupled to the proximal end of the catheter, a filter operably coupled to the distal end of the catheter, the filter movable between a collapsed and deployed position, and an actuator wire for deploying the collapsing the filter. At least a portion of the actuator wire extends within the catheter. The filter comprises a filter chassis comprising a movable collar a fixed collar and a tubular braided scaffolding coupled between the movable collar and the fixed collar. The filter chassis also comprises a filter membrane coupled to the tubular braided scaffolding.

20 Claims, 17 Drawing Sheets

Related U.S. Application Data continuation of application No. 15/005,906, filed on Jan. 25, 2016, now Pat. No. 10,292,805.

(60) Provisional application No. 62/109,388, filed on Jan. 29, 2015, provisional application No. 62/107,449, filed on Jan. 25, 2015, provisional application No. 62/107,216, filed on Jan. 23, 2015.

(56) References Cited

U.S. PATENT DOCUMENTS

| | | | |
|---|---|---|---|
| 5,108,419 A | 4/1992 | Reger et al. | |
| 5,456,667 A | 10/1995 | Ham et al. | |
| 5,913,895 A | 6/1999 | Fischell et al. | |
| 5,954,745 A | 9/1999 | Gertler et al. | |
| 6,001,118 A | 12/1999 | Daniel et al. | |
| 6,042,598 A | 3/2000 | Jang et al. | |
| 6,051,014 A | 4/2000 | Jang | |
| 6,168,579 B1 | 1/2001 | Tsugita et al. | |
| 6,179,859 B1 | 1/2001 | Bates et al. | |
| 6,258,115 B1 | 7/2001 | Dubrul et al. | |
| 6,325,815 B1 | 12/2001 | Kusleika et al. | |
| 6,344,049 B1 | 2/2002 | Levinson et al. | |
| 6,355,051 B1 | 3/2002 | Sisskind et al. | |
| 6,371,970 B1 | 4/2002 | Khosravi et al. | |
| 6,391,044 B1 | 5/2002 | Yadav et al. | |
| 6,485,502 B2 | 11/2002 | Don Michael et al. | |
| 6,511,496 B1 | 1/2003 | Huter et al. | |
| 6,511,503 B1 | 1/2003 | Burkett et al. | |
| 6,524,303 B1 | 2/2003 | Garibaldi et al. | |
| 6,537,297 B2 | 3/2003 | Tsugita et al. | |
| 6,540,722 B1 | 4/2003 | Boyle et al. | |
| 6,544,279 B1 * | 4/2003 | Hopkins | A61F 2/012 606/200 |
| 6,592,606 B2 | 7/2003 | Huter et al. | |
| 6,596,011 B2 | 7/2003 | Johnson et al. | |
| 6,607,506 B2 | 8/2003 | Kletschka et al. | |
| 6,635,084 B2 | 10/2003 | Pinchasik et al. | |
| 6,638,294 B1 | 10/2003 | Palmer et al. | |
| 6,652,557 B1 | 11/2003 | MacDonald et al. | |
| 6,656,203 B2 | 12/2003 | Roth et al. | |
| 6,656,351 B2 | 12/2003 | Boyle et al. | |
| 6,663,650 B2 | 12/2003 | Sepetka et al. | |
| 6,682,543 B2 | 1/2004 | Barbut et al. | |
| 6,702,834 B1 | 3/2004 | Boylan et al. | |
| 6,866,677 B2 | 3/2005 | Douk et al. | |
| 6,939,373 B2 | 9/2005 | Gomez et al. | |
| 6,964,673 B2 | 11/2005 | Tsugita et al. | |
| 6,969,396 B2 | 11/2005 | Krolik et al. | |
| 6,978,174 B2 | 12/2005 | Gelfand et al. | |
| 6,991,641 B2 | 1/2006 | Diaz et al. | |
| 6,994,718 B2 | 2/2006 | Groothuis et al. | |
| 7,044,958 B2 | 5/2006 | Douk et al. | |
| 7,083,633 B2 | 8/2006 | Morrill et al. | |
| 7,094,249 B1 | 8/2006 | Broome et al. | |
| 7,097,651 B2 | 8/2006 | Harrison et al. | |
| 7,137,991 B2 | 11/2006 | Fedie et al. | |
| 7,150,756 B2 | 12/2006 | Levinson et al. | |
| 7,163,549 B2 | 1/2007 | Crank et al. | |
| 7,241,305 B2 | 7/2007 | Ladd et al. | |
| 7,338,510 B2 | 3/2008 | Boylan et al. | |
| 7,422,595 B2 | 9/2008 | Morris et al. | |
| 7,481,823 B2 | 1/2009 | Broome et al. | |
| 7,653,438 B2 | 1/2010 | Demarais et al. | |
| 7,780,696 B2 | 8/2010 | Daniel et al. | |
| 7,935,075 B2 | 5/2011 | Tockman et al. | |
| 8,150,520 B2 | 4/2012 | Demarais et al. | |
| 8,303,617 B2 | 11/2012 | Brady et al. | |
| 8,372,108 B2 | 2/2013 | Lashinski et al. | |
| 8,403,976 B2 | 3/2013 | Roberts et al. | |
| 8,409,240 B2 | 4/2013 | Tripp et al. | |
| 8,518,073 B2 | 8/2013 | Lashinski et al. | |
| 8,603,131 B2 | 12/2013 | Gilson et al. | |
| 8,657,849 B2 | 2/2014 | Parker et al. | |
| 8,679,148 B2 | 3/2014 | McGuckin, Jr. et al. | |
| 8,740,930 B2 | 6/2014 | Goodwin et al. | |
| 8,758,424 B2 | 6/2014 | Sachar et al. | |
| 8,795,305 B2 | 8/2014 | Martin et al. | |
| 8,852,225 B2 | 10/2014 | Tabor et al. | |
| 8,945,169 B2 | 2/2015 | Pal | |
| 8,974,490 B2 | 3/2015 | Jönsson | |
| 9,017,364 B2 | 4/2015 | Lee et al. | |
| 9,023,077 B2 | 5/2015 | Cully et al. | |
| 2001/0012951 A1 | 8/2001 | Bates et al. | |
| 2002/0002384 A1 | 1/2002 | Gilson et al. | |
| 2002/0004667 A1 | 1/2002 | Adams et al. | |
| 2002/0062134 A1 | 5/2002 | Barbut et al. | |
| 2002/0111647 A1 | 8/2002 | Khairkhahan et al. | |
| 2002/0128680 A1 | 9/2002 | Pavlovic | |
| 2002/0138094 A1 | 9/2002 | Borillo et al. | |
| 2002/0143361 A1 | 10/2002 | Douk et al. | |
| 2002/0156457 A1 | 10/2002 | Fisher et al. | |
| 2002/0177872 A1 | 11/2002 | Papp et al. | |
| 2003/0004536 A1 | 1/2003 | Boylan et al. | |
| 2003/0040772 A1 | 2/2003 | Hyodoh et al. | |
| 2003/0055480 A1 | 3/2003 | Fischell et al. | |
| 2003/0060843 A1 | 3/2003 | Boucher et al. | |
| 2003/0065354 A1 | 4/2003 | Boyle et al. | |
| 2003/0083736 A1 | 5/2003 | Brown et al. | |
| 2003/0093106 A1 | 5/2003 | Brady et al. | |
| 2003/0139764 A1 | 7/2003 | Levinson et al. | |
| 2003/0167084 A1 | 9/2003 | Orlowski et al. | |
| 2003/0176884 A1 | 9/2003 | Berrada et al. | |
| 2003/0212361 A1 | 11/2003 | Boyle et al. | |
| 2003/0216792 A1 | 11/2003 | Levin et al. | |
| 2003/0220665 A1 | 11/2003 | Eskuri et al. | |
| 2003/0225435 A1 | 12/2003 | Huter et al. | |
| 2004/0054322 A1 | 3/2004 | Vargas et al. | |
| 2004/0082967 A1 | 4/2004 | Broome et al. | |
| 2004/0111111 A1 | 6/2004 | Lin et al. | |
| 2004/0122466 A1 | 6/2004 | Bales et al. | |
| 2004/0158280 A1 | 8/2004 | Morris et al. | |
| 2004/0167564 A1 | 8/2004 | Fedie et al. | |
| 2004/0172128 A1 | 9/2004 | Hong et al. | |
| 2004/0215332 A1 | 10/2004 | Frid | |
| 2004/0260387 A1 | 12/2004 | Regala et al. | |
| 2005/0015111 A1 | 1/2005 | McGuckin et al. | |
| 2005/0038468 A1 | 2/2005 | Panetta et al. | |
| 2005/0119668 A1 | 6/2005 | Teague et al. | |
| 2005/0228438 A1 | 10/2005 | Sachar et al. | |
| 2005/0288730 A1 | 12/2005 | Deem et al. | |
| 2006/0015139 A1 | 1/2006 | Tsugita et al. | |
| 2006/0041277 A1 | 2/2006 | Deem et al. | |
| 2006/0100658 A1 | 5/2006 | Obana et al. | |
| 2006/0129130 A1 | 6/2006 | Tal et al. | |
| 2006/0129180 A1 | 6/2006 | Tsugita et al. | |
| 2006/0142801 A1 | 6/2006 | Demarais et al. | |
| 2006/0235474 A1 | 10/2006 | Demarais et al. | |
| 2006/0241735 A1 | 10/2006 | Tockman et al. | |
| 2007/0043306 A1 | 2/2007 | Olson et al. | |
| 2007/0061418 A1 | 3/2007 | Berg et al. | |
| 2007/0123926 A1 | 5/2007 | Sater et al. | |
| 2007/0156168 A1 | 7/2007 | Dunfee et al. | |
| 2007/0167975 A1 | 7/2007 | Boyle et al. | |
| 2007/0208373 A1 | 9/2007 | Zaver et al. | |
| 2007/0299466 A1 | 12/2007 | Sachar et al. | |
| 2008/0097399 A1 | 4/2008 | Sachar et al. | |
| 2010/0010534 A1 | 1/2010 | Mujkanovic et al. | |
| 2010/0106182 A1 | 4/2010 | Patel et al. | |
| 2010/0286722 A1 | 11/2010 | Rizk et al. | |
| 2011/0004291 A1 | 1/2011 | Davis et al. | |
| 2011/0071619 A1 | 3/2011 | Bliss et al. | |
| 2011/0130657 A1 | 6/2011 | Chomas et al. | |
| 2011/0137399 A1 | 6/2011 | Chomas et al. | |
| 2011/0152993 A1 | 6/2011 | Marchand et al. | |
| 2011/0207999 A1 | 8/2011 | Torisawa et al. | |
| 2012/0089102 A1 | 4/2012 | Chomas et al. | |
| 2012/0150211 A1 | 6/2012 | Galdonik et al. | |
| 2012/0330402 A1 | 12/2012 | Vad et al. | |
| 2013/0031087 A1 | 1/2013 | Kropitz et al. | |
| 2013/0226225 A1 | 8/2013 | Sachar et al. | |
| 2013/0310871 A1 | 11/2013 | Sachar et al. | |
| 2014/0052170 A1 | 2/2014 | Heuser et al. | |
| 2014/0135661 A1 | 5/2014 | Garrison et al. | |

(56) References Cited

U.S. PATENT DOCUMENTS

| | | |
|---|---|---|
| 2014/0214067 A1 | 7/2014 | Sachar et al. |
| 2014/0228820 A1 | 8/2014 | Blaskowski et al. |
| 2014/0277383 A1 | 9/2014 | Sachar et al. |
| 2014/0343663 A1 | 11/2014 | Mayer et al. |
| 2015/0018928 A1 | 1/2015 | Sachar et al. |
| 2015/0025567 A1 | 1/2015 | Ren et al. |
| 2015/0133918 A1 | 5/2015 | Sachar |

FOREIGN PATENT DOCUMENTS

| | | | |
|---|---|---|---|
| JP | 2013154183 A | | 8/2013 |
| WO | 0067665 A1 | | 11/2000 |
| WO | 0067669 A1 | | 11/2000 |
| WO | 2004087249 A2 | | 10/2004 |
| WO | 2004096089 A2 | | 11/2004 |
| WO | 2005004968 A1 | | 1/2005 |
| WO | 2007061418 A2 | | 5/2007 |
| WO | 2007136669 A2 | | 11/2007 |
| WO | 2009517124 A | | 4/2009 |
| WO | 2009126747 A1 | | 10/2009 |
| WO | 2009151761 A1 | | 12/2009 |
| WO | 2010/014515 A2 | | 2/2010 |
| WO | 2011517424 A | | 6/2011 |
| WO | 2014085590 A1 | | 6/2014 |
| WO | 2014144787 A1 | | 9/2014 |
| WO | 2014150013 A1 | | 9/2014 |
| WO | 2015070147 A1 | | 5/2015 |
| WO | 2016502443 A | | 1/2016 |

OTHER PUBLICATIONS

Extended European Search Report. Application No. EP 16740903.6. dated Aug. 9, 2018. 9 pages.
Extended EP Search Report issued in Application No. EP 13857790. 3, dated Jun. 9, 2016, 9 pages.
Final Office Action issued in U.S. Appl. No. 14/537,397, dated Jan. 25, 2018.
Final Office Action issued in U.S. Appl. No. 14/091,903, dated Jun. 22, 2018.
Non-Final Office Action issued in U.S. Appl. No. 14/091,903, dated Dec. 28, 2017.
Office Action issued in U.S. Appl. No. 14/091,903, dated Mar. 1, 2017.
Non-Final Office Action issued in U.S. Appl. No. 14/091,903, dated Sep. 13, 2016.
Non-Final Office Action issued in U.S. Appl. No. 14/537,397, dated Jul. 13, 2017.
Office Action issued by Japanese Patent Office in Application No. 2017-038064 dated Sep. 11, 2018, 5 pages, with Machine Translation of same, 4 pages.
European Search Report and Written Opinion dated Oct. 7, 2011 for EP Application No. 05852233.5, 7 pages, dated Oct. 7, 2011.
Extended European Search Report, European Application No. 14859919. 4, dated Aug. 30, 2017.
International Search Report and Written Opinion of the International Searching Authority, Application No. PCT/US2013/072232, 6 pages, dated Feb. 18, 2014.
International Search Report and Written Opinion of the International Searching Authority, Application No. PCT/US2014/064817, 6 pages, dated Feb. 23, 2015.
International Search Report and Written Opinion of the International Searching Authority, Application No. PCT/US2005/042826, 5 pages, dated Jun. 28, 2007.
International Search Report and Written Opinion of the International Searching Authority, Application No. PCT/US2014/021850, 9 pages, Jul. 21, 2014.
International Search Report and Written Opinion of the International Searching Authority, Application No. PCT/US2014/029342, 6 pages, dated Aug. 19, 2014.
International Search Report and Written Opinion of the International Searching Authority, Application No. PCT/US2009/040202, 6 pages, dated Nov. 5, 2009.
"Mounted," American Webster Dictionary, http://dictionary.reference. com/browse/mounted, Jan. 28, 2007.
Ansel, G.M. et al., "Carotid stenting with embolic protection: evolutionary advances," Expert Rev Med Devices (2008) 5(4):427-436.
Baim, Donald S. et al., "Randomized trial of a distal embolic protection device during percutaneous intervention of saphenous vein aorto-coronary bypass grafts", Circulation 105.11, 2002, 1285-1290.
Barbato, "A randomized trial of carotid artery stenting with and without cerebral protection" J Vasc Surg (Apr. 2008) 47(4): 760-765.
Bijuklic, et al., "The PROFI Study (Prevention of Cerebral Embolization by Proximal Balloon Occlusion Compared to Filter Protection During Carotid Artery Stenting): a perspective randomized trail", J Am Coll Cardiel (Apr. 10, 2012) 59(15): 1383-1389.
Charalambous, et al., "Reduction of Cerebral Embolization in Carotid Angioplasty: An In-Vitro Experiment Comparing 2 Cerebral Protection Devices", J Endovasc Ther (Apr. 2009) 16(2): 161-167.
Eskandari, , "Cerebral Embolic Protection", Semin Vasc Surg (Jun. 2005) 18(2): 95-100.
Karada, et al., "Significance of Combining Distal Filter Protection and a Guiding Catheter With Temporary Balloon Occlusion for Carotid Artery Stenting: Clinical Results and Evaluation of Debris Capture", Ann Vasc Surg (Oct. 2012) 26(7): 929-936.
Kasirajan et al., "Filter devices for cerebral for cerebral protection during carotid angioplasty and stenting" J Endovasc Ther (Dec. 2003) 10(6): 1039-1045.
Kumar et al. "Effects of Design Parameters on the Radial Force of Percutaneous Aortic Valve Stents," Cardiovasc Revasc Med 2010 11(2): 101-104.
Mathias, "Carotid artery stenting with filters" J Cardiovasc Surg (Torino) (Feb. 2013) 54(2)): 33-39.
MacDonald "Is there any evidence that cerebral protection is beneficial? Experimental data" J Cardiovasc Surg (Torino) (2006) 47(2): 127-136.
Muller-Hulsbeck, et al., In vitro comparison of four cerebral protection filters for preventing human plaque embolization during carotid interventions,: J Endovasc Ther (Dec. 2002) 9(6): 793-802.
Ohki, et al., "Critical Analysis of Distal Protection Devices", Semin Vasc Surg (Dec. 2003) 16(4): 317-325.
Order, et al., "Comparison of 4 Cerebral Protection Filters for Carotid Angioplasty: An In Vitro Experiment Focusing on Carotid Anatomy", J Endovasc Ther (Apr. 2004) 11(2): 211-218.
International Search Report and Written Opinion issued in PCT/US15/52360 dated Dec. 22, 2015.
International Search Report and Written Opinion issued in PCT/US16/14763, dated Jul. 5, 2016.
Roberts, et al., Effective endovascular treatment of calcified femoropopliteal disease with directional atherectomy and distal embolic protection: Final Results of the DEFINITIVE Ca++ Trial. Catheterization and Cardiovascular Interventions. vol. 84 (2014) pp. 236-244.
Sharma, et al., Selection of Guide Wires and Specialty Devices, Apr. 2014, 90 pages (also available on-line at http://cccsymposium.org/2014-interventional_card-ppts/06-10-14_12-30_sharma.pdf).
First Examination Report issued by the Australian Intellectual Property Office in Australian Application No. 2016209053 dated Sep. 5, 2019. 4 pages.
Second Examination Report issued by the Australian Intellectual Property Office in Australian Application No. 2016209053 dated Mar. 11, 2020. 2 pages.
Decision of Rejection issued by the Japanese Patent Office in Japanese Application No. 2017-038064 dated Jul. 2, 2019. 5 pages including English summary of Decision of Rejection.
Decision of Rejection issued by the Japanese Patent Office in Japanese Application No. 2017-538714 dated Oct. 29, 2019. 7 pages including English summary of Decision of Rejection.

(56) References Cited

OTHER PUBLICATIONS

Office Action issued by the Brazilian Institute of Industrial Property in Brazilian Application No. BR112015012317-1 dated Dec. 2, 2019. 6 pages including English summary of Office Action.
Japanese Patent Office. Office Action issued in Japanese Application No. 2020-016328 dated Mar. 26, 2021. 10 pages, including English translation.
Examination Report issued for Indian Application No. 5673/DELNP/2015, dated Feb. 11, 2020.
Office Action issued for Canadian Application No. 2,974,532, dated Jan. 25, 2022. 11 pages.

* cited by examiner

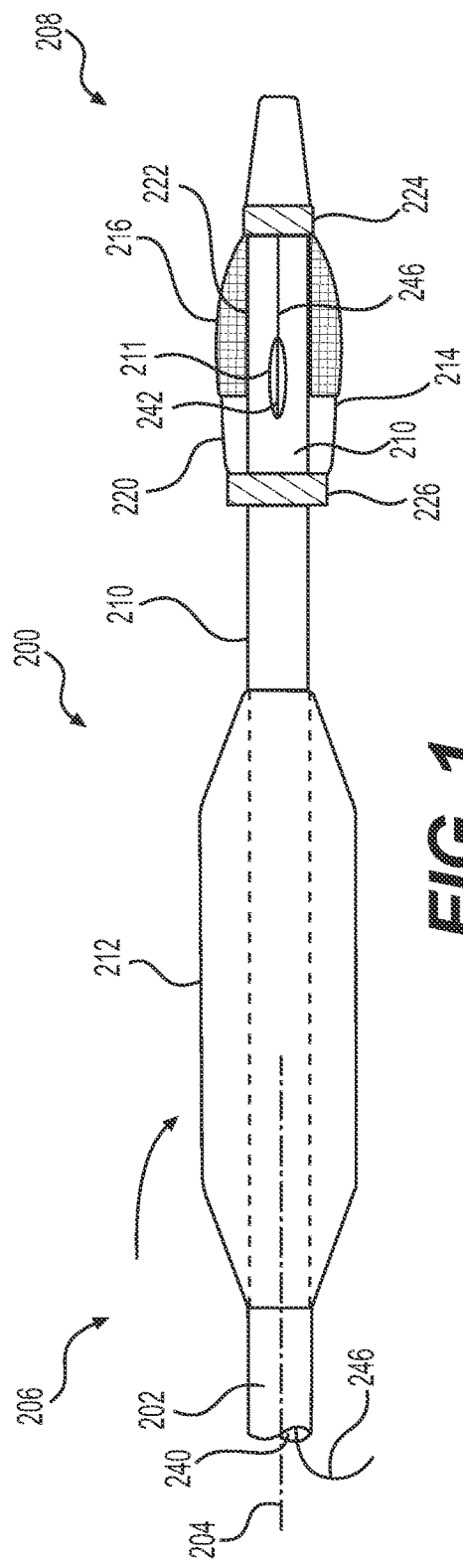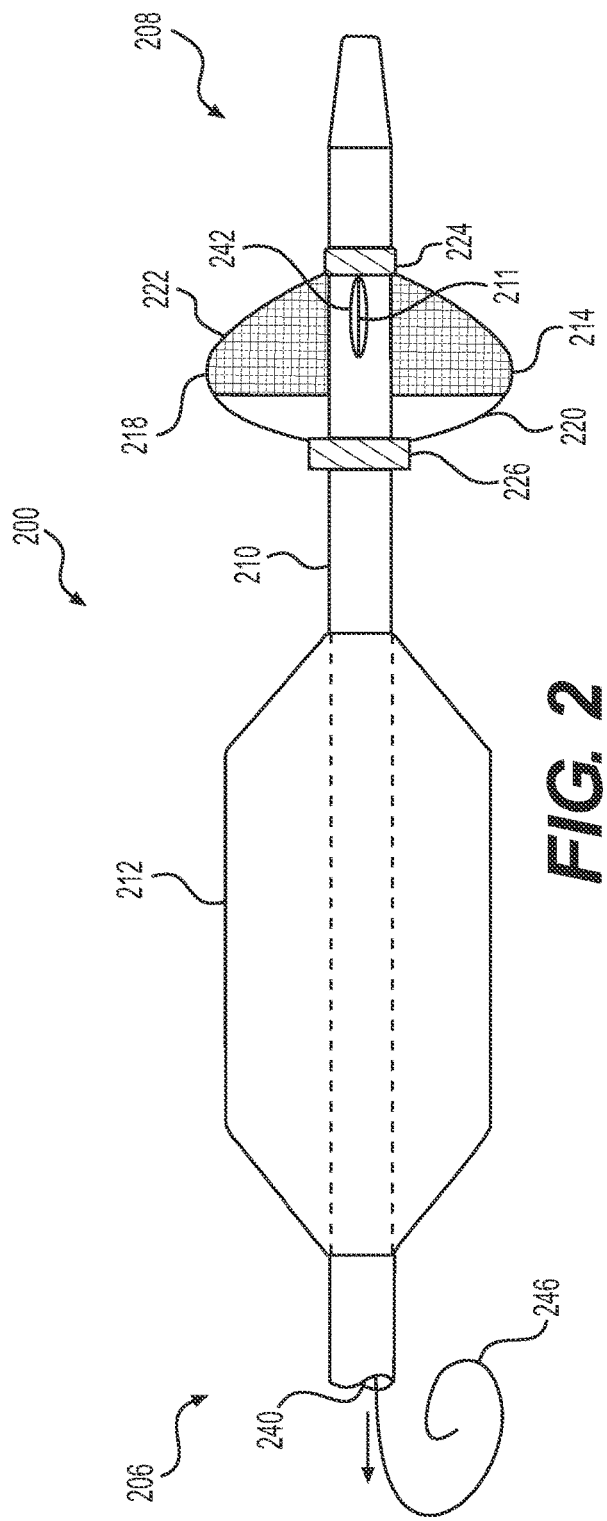

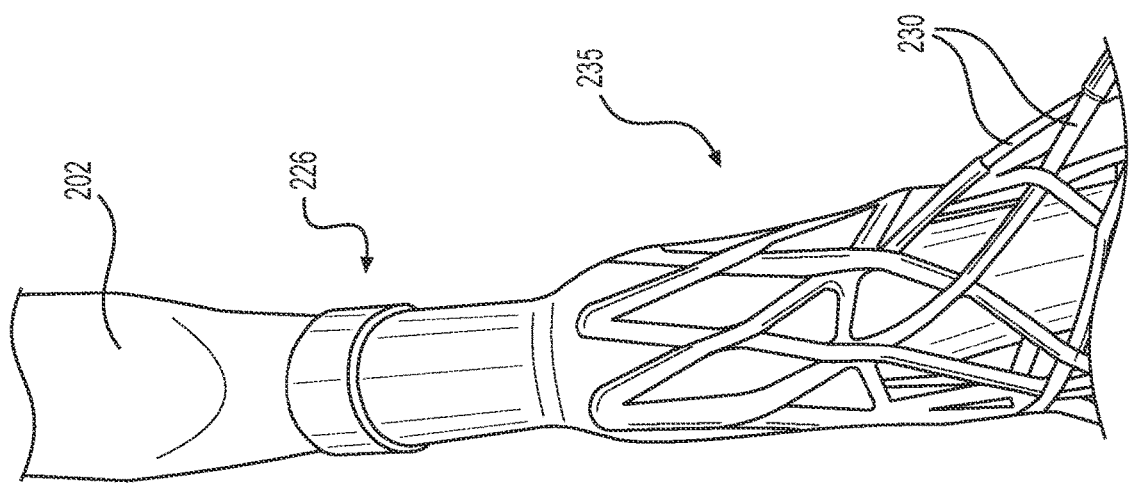
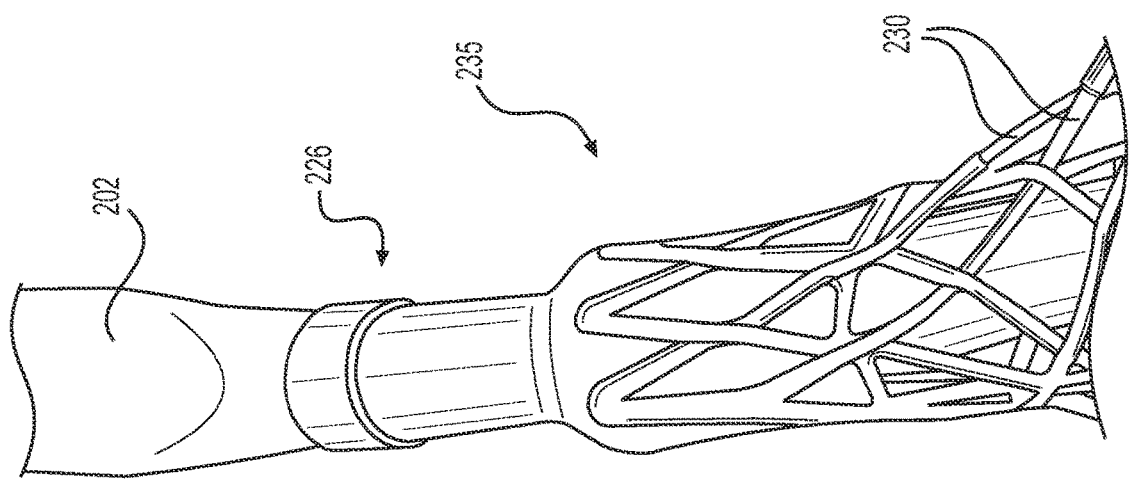
FIG. 7

MEMBRANE PARTICULATE CAPTURE EFFICIENCY TEST RESULTS

| SAMPLE | START FLOW RATE (mL/min) | DEPLOYED FILTER FLOW RATE (mL/min) | CAPTURE PERCENTAGE |
|---|---|---|---|
| 1 | 111.85 | 112.22 | 100% |
| 2 | 92.2 | 93.7 | 100% |
| 3 | 111.46 | 111.26 | 100% |
| 4 | 114.5 | 115.28 | 100% |
| 5 | 110.0 | 109.92 | 100% |
| 6 | 113.72 | 114.0 | 100% |
| 7 | 111.1 | 111.4 | 100% |
| 8 | 108.4 | 105.5 | 100% |
| 9 | 110.06 | 109.92 | 100% |
| 10 | 109.2 | 110.0 | 100% |
| 11 | 109.8 | 108.6 | 100% |
| 12 | 111.6 | 109.2 | 100% |
| 13 | 111.6 | 110.6 | 100% |
| 14 | 107.4 | 107.0 | 100% |
| 15 | 107.2 | 107.0 | 100% |

*FIG. 17*

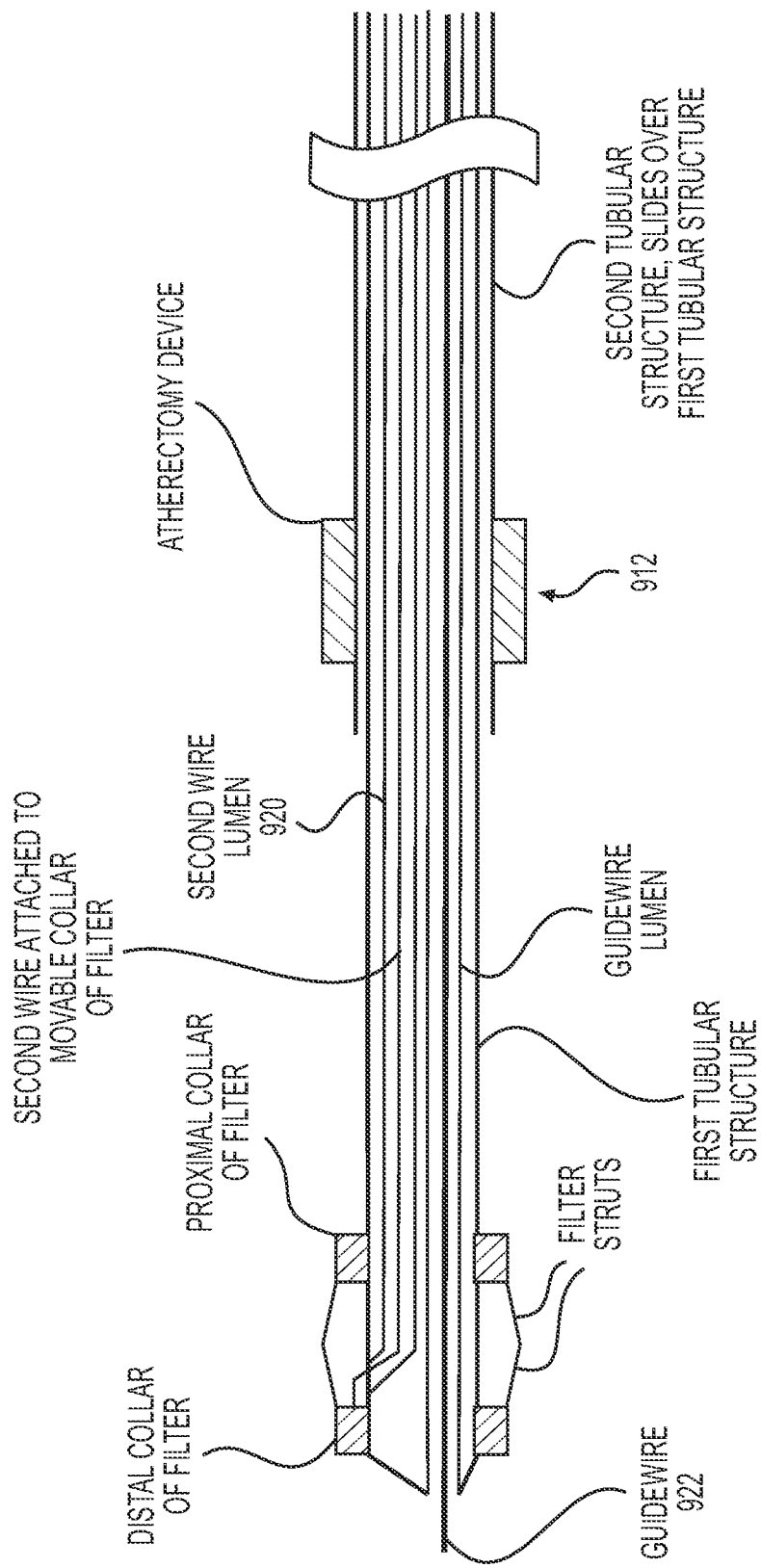

INTERVENTIONAL DEVICE HAVING AN INTEGRATED EMBOLIC FILTER AND ASSOCIATED METHODS

RELATED APPLICATIONS

This application is a continuation application of U.S. Pat. No. 11,166,802, filed Apr. 10, 2019 and issued Nov. 9, 2021. U.S. Pat. No. 11,166,802 is a continuation application of U.S. Pat. No. 10,292,805, filed Jan. 25, 2016 and issued May 21, 2019, which claims the benefit of U.S. Provisional Application 62/107,216, filed Jan. 23, 2015, U.S. Provisional Application 62/107,449, filed Jan. 25, 2015, and U.S. Provisional Application 62/109,388, filed Jan. 29, 2015. Each of these applications are incorporated by reference in their entireties for all purposes.

BACKGROUND OF THE INVENTION

Field of the Invention

This invention relates generally to interventional devices and, more particularly, to interventional devices having an integrated embolic filter, as well as methods of making and using the same.

Description of the Related Art

The vascular bed supplies a constant flow of oxygen-rich blood to the organs. In diseased vessels, blockages can develop that can reduce blood flow to the organs and cause adverse clinical symptoms up to and including fatality. Diseased vessels can comprise a range of material from early-stage thrombosis to late-stage calcified plaque.

Angioplasty can be described as a catheter-based procedure performed by a physician to open a stenosed vessel and restore blood flow. An entry site can be opened, for example, in the patient's groin, arm, or hand, and a guide wire and catheter can be advanced under fluoroscopic guidance to the location of the blockage. A catheter having a small balloon adjacent its distal end can be advanced under fluoroscopic guidance until the balloon lies within the stenosed region. The balloon can be then inflated and deflated one or more times to expand the stenosed region of the artery.

Angioplasty is one example of a vascular intervention that can release embolic particles down-stream from a stenosed or otherwise compromised location during intervention. These embolic particles can result in adverse clinical consequences. It has been shown beneficial to trap these embolic particles to prevent them from traveling downstream with blood flow to the capillary bed (e.g., Balm D S, Wahr D, George B, et al., Randomized trial of a distal embolic protection device during percutaneous intervention of saphenous vein aorta-coronary bypass grafts, Circulation 2002; 105:1285-90).

In addition to balloon angioplasty, stenoses can also be treated with stents and with mechanical thrombectomy devices. These devices are also prone to releasing embolic particles downstream from a stenosed location during intervention.

Systems available today used to catch these embolic particles consist primarily of distal filter systems or occlusion balloon systems. Distal filter systems are on guidewires, as are distal balloon occlusion systems. Proximal balloon occlusion systems are on a guide catheter or sheath. These systems suffer shortcomings related to simplicity of use. Embolic protection guidewires also suffer from flexibility and stability problems that render the protected angioplasty procedure relatively more difficult in many cases. In the case of saphenous vein grafts, the problems relate specifically to aorto-ostial lesions, where the guidewire may not be long enough to provide support, or distal vein graft lesions, where there can be not enough of a landing zone for the filter. The latter can be a problem as currently available filter systems can have a considerable distance between the treatment balloon and the distal filter. This distance can be a problem not only in distal vein graft lesions, but also in arterial stenoses in which there can be a side branch immediately after the stenosis. In such cases, the filler can often be deployed only distal to the side branch, thus leaving the side branch unprotected from embolic particles.

Accordingly, a need exists for improved interventional devices having an integrated embolic filter as well as methods for making an using the same.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, the present disclosure describes a percutaneous, transluminal angioplasty device comprising an elongated catheter having a longitudinal axis, a proximal end portion, a distal end portion and an outer side wall. In one aspect, an interventional device can be operably coupled to the proximal end portion of the catheter. In one aspect, a filter can be operably coupled to the distal end portion of the catheter, the filter movable between a collapsed position and a deployed position. The filter can comprise a filter chassis. In one aspect, the chassis can comprise a movable collar slidably coupled to the catheter, and a fixed collar spaced from the movable collar relative to the longitudinal axis of the catheter. The fixed collar can be immovably coupled to the catheter. In one aspect, the percutaneous, transluminal angioplasty device can have, a tubular braided scaffolding. In one aspect, the tubular braided scaffolding can have a first end coupled to the movable collar and an opposed second end coupled to the fixed collar. In one aspect, the percutaneous, transluminal angioplasty device can comprise a filter membrane coupled to the tubular braided scaffolding and extending to at least the distal end of the filter chassis. The filter membrane can comprise a mesh size of from 40 microns to 100 microns. In one aspect, the percutaneous, transluminal angioplasty device can comprise an actuator wire, at least a portion of the actuator wire extending within the catheter, a distal end of the actuator wire exiting the catheter through a port provided on an outer side wall of the catheter, and a distal end of the actuator wire being coupled to the movable collar. In one aspect, the percutaneous, transluminal angioplasty device can comprise a handle coupled to the proximal end portion of the catheter and operably coupled to a proximal end of the actuator wire at a screw, and an actuator coupled to the screw. The activation of the actuator can effect axial displacement of the screw, and correspondingly, the actuator wire, relative to a longitudinal axis of the handle. In one aspect, the rotation of the screw causes the actuator wire to move along the longitudinal axis of the catheter, where movement of the actuator wire causes the filter to move between the collapsed position and the deployed position by exerting a force on and moving the movable collar relative to the fixed collar along the longitudinal axis of the catheter.

In another aspect, the tubular braided scaffolding can comprise a plurality of wire cross-overs along each of a plurality of wires. When traveling along a selected wire, the plurality of wires extending transverse to the selected wire cross the selected wire in a repeating sequence of one transverse wire over the selected wire followed by one transverse wire under the selected wire.

In another aspect, the tubular braided scaffolding can comprise a plurality of wire cross-overs along each of a plurality of wires. When traveling along a selected wire, the plurality of wires extending transverse to the selected wire cross the selected wire in a repeating sequence of two transverse wires over the selected wire followed by one transverse wire under the selected wire.

In another aspect, the filter membrane can comprise a mesh size of from 40 microns to 60 microns.

In another aspect, the tubular braided scaffolding has a shape memory of the collapsed position and movement of the actuator wire causes the filter to expand to the deployed position.

In another aspect, during a first rotational direction of the screw, the movable collar is displaced toward the fixed collar, expanding the filter towards the deployed position, and during a second rotational direction of the screw, the movable collar is displaced away from the fixed collar, moving the filter towards the collapsed position.

In another aspect, the filter in the deployed position captures embolic particles having a particle size of at least 40 microns.

In another aspect, when the filter is in the deployed position, the filter chassis is sized and configured to conform to a shape of a target vessel over a length of the target vessel.

In another aspect, the tubular braided scaffolding can further comprise a plurality of wires and each wire of the plurality of wires moves independently with respect to the other wires between the movable collar and the fixed collar as the filter moves between the collapsed position and the deployed position.

In another aspect, the tubular braided scaffolding includes from about 6 to about 20 wire crossover portions per inch along a length of at least one of the plurality of wires.

In another aspect, a crossover portion of a wire of the plurality of wires slidably contacts another wire of the plurality of wires as the filter moves between the collapsed position and the deployed position.

In another aspect, the tubular braided scaffolding can comprise at least one cross over portion and the at least one non-cross over portion, and the filter membrane is coupled to at least one non-crossover portion of the tubular braided scaffolding.

In another aspect, the tubular braded scaffolding can comprise at least one cross over portion and the at least one non-cross over portion, and the filter membrane is coupled to a non-crossover portion provided at a location adjacent to a maximum radial displacement of the filter chassis when in the deployed position.

In another aspect, the filter membrane extends beyond the filter chassis in a longitudinal direction relative to the longitudinal axis of the catheter.

In another aspect, the interventional device is an angioplasty device, the angioplasty device can include at least one of an angioplasty balloon, a stent, a mechanical thrombectomy device, an atherectomy device, a valvuloplasty device, or an ablation device.

In another aspect the present disclosure describes a method of filtering embolic particles during an angioplasty procedure, the method can comprise guiding a catheter through a vascular system of a subject. In one aspect, the method can comprise positioning an embolic filter attached to the catheter downstream of a blocked or partially blocked region of a blood vessel. In one aspect, the method can comprise positioning an angioplasty device attached to the catheter within the blocked or partially blocked region of the blood vessel. In one aspect, the method can comprise moving an actuator wire attached to a movable side of the embolic filter in a first direction, thereby overcoming a self-collapsing bias within the embolic filter and opening the embolic filter to an expanded position within the blood vessel. In one aspect, the method can comprise expanding the angioplasty device against the blocked or partially blocked region of the blood vessel. In one aspect, the method can comprise capturing embolic particles against a filter membrane of the embolic filter. The filter membrane can comprise a mesh size of from 40 microns to 100 microns. In one aspect, the method can comprise collapsing the angioplasty device. In one aspect, the method can comprise moving the actuator wire attached to the movable side of the embolic filter in a second direction that is opposite to the first direction, thereby allowing the self-collapsing bias within the embolic filter to close the embolic filter. In one aspect, the method can comprise removing the catheter, embolic filter, and angioplasty device from the vascular system of the subject.

In another aspect, the method of filtering embolic particles can comprise maintaining the embolic filter in the expanded position for a time period of 5 minutes or less.

In another aspect, the filter membrane can comprise a mesh size of from 40 microns to 60 microns.

In another aspect, the angioplasty device is an angioplasty balloon. Expanding the angioplasty device can comprise inflating the angioplasty balloon, and collapsing the angioplasty device can comprise deflating the angioplasty balloon.

In another aspect, moving the actuator wire attached to the movable side of the embolic filter in the first direction can further comprise pulling the actuator wire in a proximal direction.

In another aspect, moving the actuator wire attached to the movable side of the embolic filter in the first direction can further comprise rotating an actuator positioned adjacent to a proximal end portion of the catheter and attached to a proximal end of the actuator wire.

In another aspect, the movable side of the embolic filter is movably attached to the catheter. The fixed side of the embolic filter is fixedly attached to the catheter. Overcoming a self-collapsing bias within the embolic filter and opening the embolic filter to an expanded position can further comprise moving the movable side of the embolic filter toward a fixed side of the embolic filter.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following descrip-

BRIEF DESCRIPTION OF THE DRAWINGS

The accompanying drawings, which are incorporated in and constitute a part of this specification, illustrate aspects and together with the description, serve to explain the principles of the methods and systems.

FIG. 1 provides a side view of an example percutaneous transluminal device illustrating the filter in a collapsed position;

FIG. 2 provides a side view of the percutaneous transluminal device of FIG. 1 illustrating the filter in a deployed position;

FIG. 7 provides two partial side views of the percutaneous transluminal device and deployed filter of FIG. 3 with varied braid configurations;

FIG. 17 provides a table of Membrane Particulate Capture Efficiency Test Results;

FIG. 20 provides an example percutaneous transluminal device.

DESCRIPTION OF THE INVENTION

Figure 3:
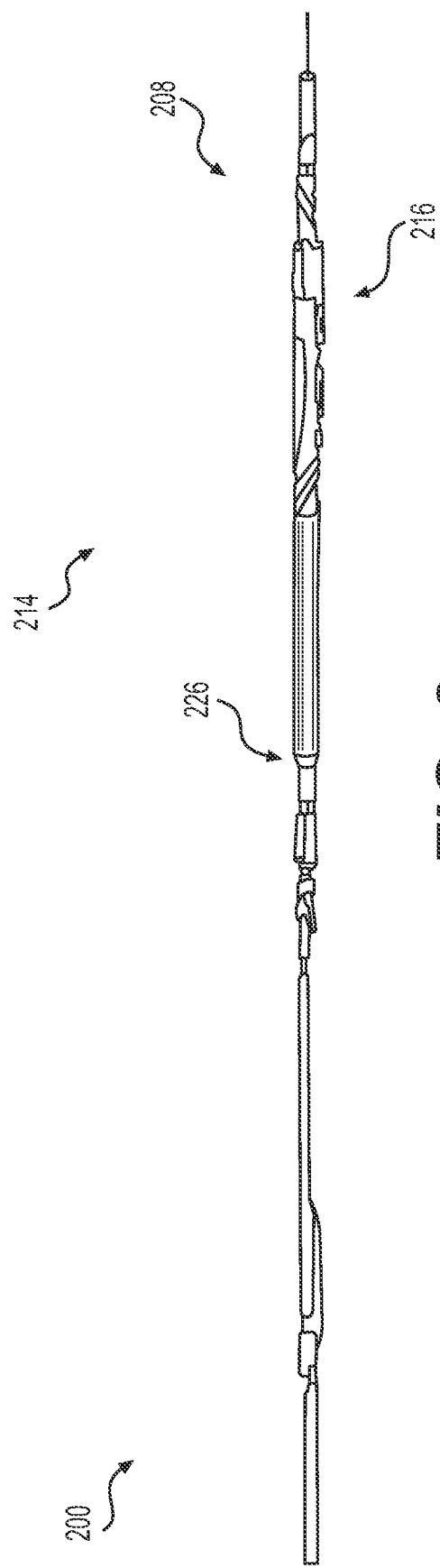
FIG. 3 provides a side view of an example percutaneous transluminal device illustrating the filter in a collapsed position.
Figure 4:
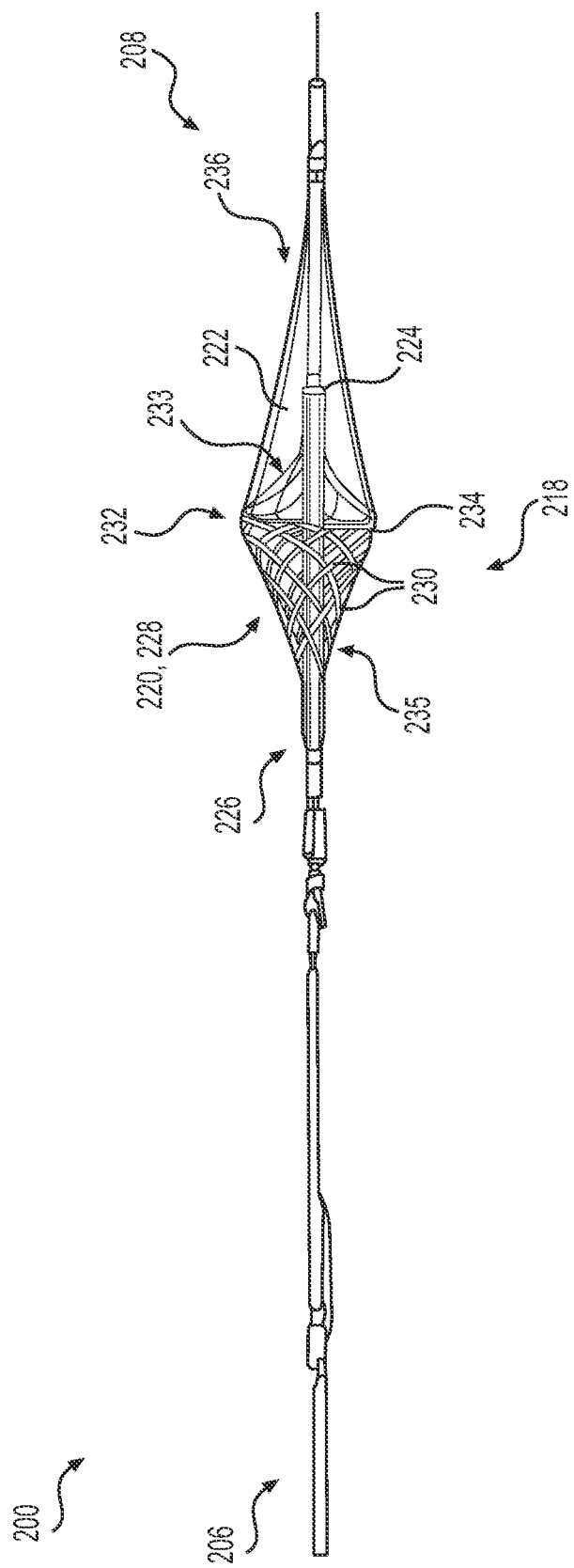
FIG. 4 provides a side view of the percutaneous transluminal device of FIG. 3 illustrating the filter in a deployed position.
Figure 5:
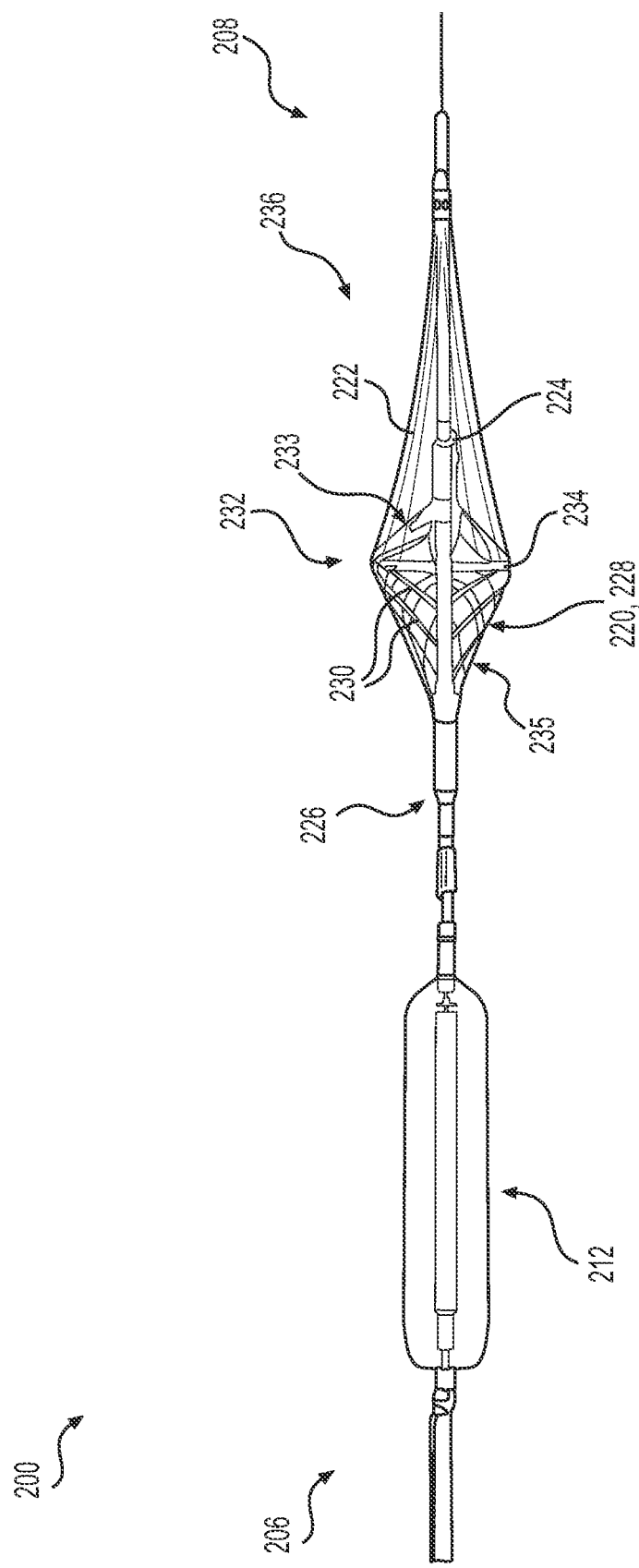
FIG. 5 provides a side view of the percutaneous transluminal device of FIG. 3 illustrating the filter and the interventional device in deployed positions.
Figure 6:
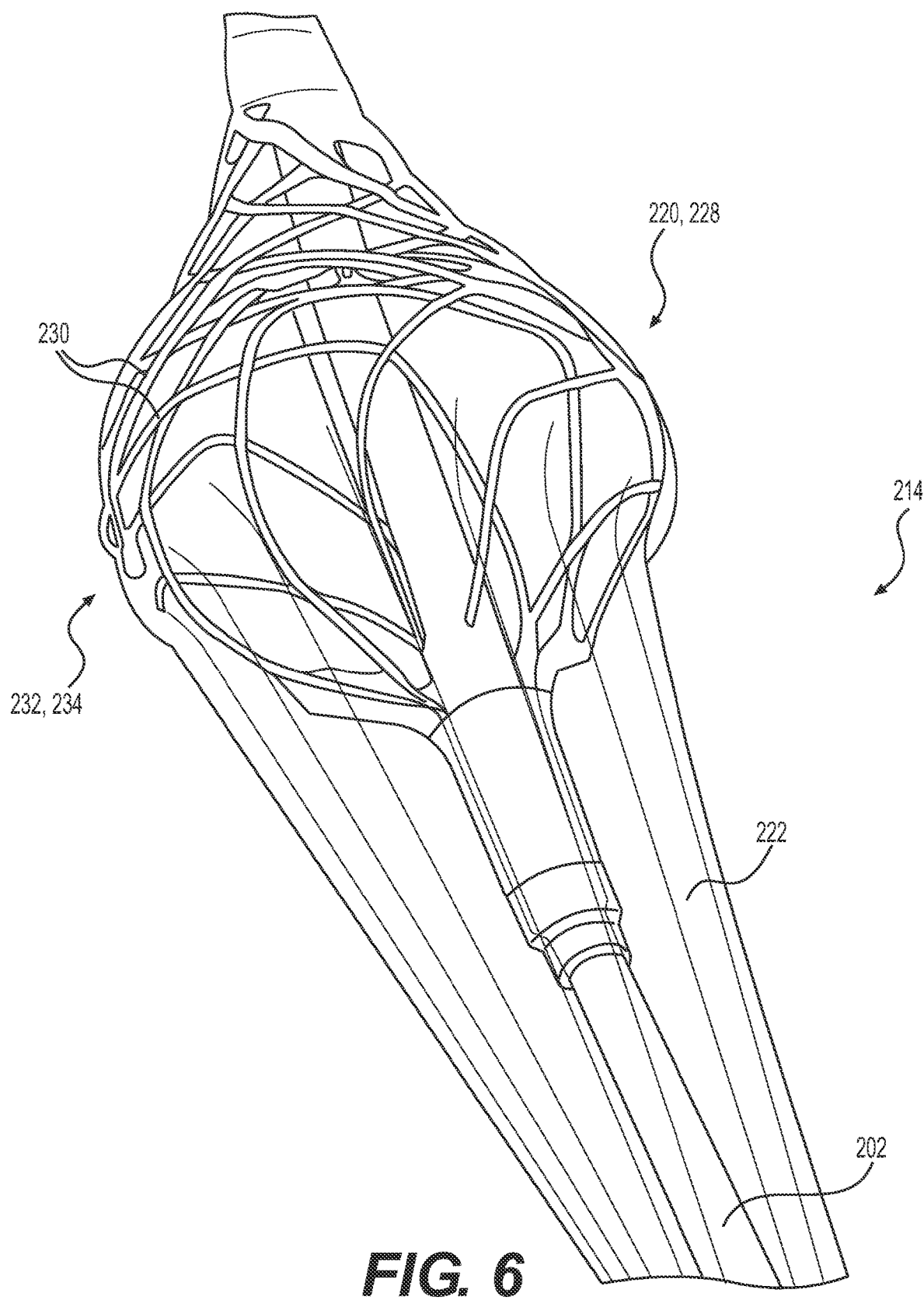
FIG. 6 provides a partial perspective view of the percutaneous transluminal device and deployed filter of FIG. 3.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well-known aspects of vascular intervention and vascular interventional devices have not been described in particular detail in order to avoid unnecessarily obscuring aspects of the disclosed implementations.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be predefined it is understood that each of these additional steps can be predefined with any specific aspect or combination of aspects of the disclosed methods.

Implementations described herein and depicted in FIGS. 1-15 provide for a percutaneous transluminal catheter-based device comprising an interventional device and having an integrated filter. The integrated filter comprises a flexible and conformable braided filter chassis that enables the filter to conform to any vessel shape. Additionally, the integrated filter can be configured to selectively move about and between a collapsed position and a deployed position. In another aspect, the unconstrained diameter of the filter in the deployed position can be greater than the target vessel. Accordingly, the integrated filter can be selectively deployed to conformably oppose the vessel wall and create a zone of apposition between the filter and the vessel wall. The devices described herein enable many other advantages over prior art devices, such as improved flexibility, a lower profile, no buckling even in the most tortuous vascular segments, improved traction through bends and pre-existing stents in steep angles, atraumatic deployment, 100% embolic capture efficiency, and complete collapse to facilitate ease and predictability of removal. These features and advantages, along with other features and advantages, will be discussed in detail herein.

In another aspect, the interventional device 212 can be an angioplasty interventional device such as, for example and without limitation, an angioplasty balloon, a stent, a mechanical thrombectomy device, an atherectomy device and the like. In a further aspect, the atherectomy device can comprise a rotational atherectomy device, a directional atherectomy device or a combination thereof. In other aspects, the interventional device can be selected to effect valvuloplasty, ablation, or the like.

In one aspect illustrated in FIGS. 1-7, the present disclosure describes a percutaneous transluminal device 200 comprising an elongated catheter 202 having a longitudinal axis 204, a proximal end portion 206, a distal end portion 208, and an outer side wall 210; an interventional device 212 operably coupled to the proximal end portion 206 of the catheter 202, and a filter 214 operably coupled to the distal end portion 208 of the catheter 202, wherein the filter 214 can be selectively collapsible and expandable about and between a collapsed position 216 and a deployed position 218. An exemplary interventional device is shown in a deployed position in FIG. 5. In light of the present disclosure, one skilled in the art will appreciate that the interventional device 212 can be located either proximal or distal to the filter 214 relative to the longitudinal axis 204 of the catheter 202 depending on the particulars of the intervention for which the percutaneous transluminal device 200 is configured to effect. Similarly, one skilled in the art will understand that the filter 214 should be oriented appropriately and located downstream from the interventional device 212 relative to the blood flow depending on the same. Solely for clarity of disclosure, the specific case of angioplasty and a treatment device comprising a filter located distal to the treatment device is described and discussed herein; accordingly, neither of these features should be construed as limiting aspects of this disclosure.

In another aspect, the filter 214 can comprise a filter chassis 220 and a filter membrane 222 operably coupled to the filter chassis 220. In one aspect, the filter chassis 220 can comprise a movable collar 224 slidably coupled to the catheter 202, a fixed collar 226 spaced from the movable collar 224 relative to the longitudinal axis 204 of the catheter 202 and immovably coupled to the catheter 202, and a tubular braided scaffolding 228 comprising a plurality of wires 230 and having a first end 233 coupled to the movable collar 224 and an opposed second end 235 coupled to the fixed collar 226. It is contemplated that each wire of the plurality of wires 230 of the tubular braided scaffolding 228 extends between the first and second ends of the braided scaffolding 228. In another aspect, each wire of the plurality of wires moves independently, or, alternatively, slides independently, with respect to the other wires between the movable collar and the fixed collar as the filter moves between the collapsed position 216 and the deployed position 218. In operation, as the distance between the movable collar 224 and the fixed collar 226 along the catheter longitudinal axis 204 is selectively decreased, a central 40 portion 232 of the tubular braided scaffolding 228 will radially expand, causing the filter 214 to selectively expand towards the deployed position 218 and conformably appose an inner wall of the target vessel thus achieving atraumatic filter deployment. As one skilled in the art will appreciate in light of the present disclosure, the filter chassis 220 described herein enables the filter 214 to conform to the shape of the vessel and, when the at least partially deployed filter radius 234 is greater than the target vessel radius, conformably appose the vessel wall over a length referred to herein as a "zone of apposition" thereby increasing the capture efficiency of the deployed filter. Additionally, one skilled in the art will appreciate in light of the present disclosure that the filter chassis 220 described herein can collapse completely against the catheter side wall when the filter 214 is returned to the collapsed position 216 and, also, will not buckle regardless of vessel tortuosity.

In another aspect, the plurality of wires 230 comprises from about 12 to about 64 wires, more particularly, from about 12 to about 32 wires, and, most particularly, about 16 wires.

In another aspect, each of the plurality of wires 230 can be formed from a shape memory material. It is contemplated that the shape memory material can be, for example and without limitation, nitinol or any other shape memory material known in the art. In a further aspect, the braided scaffolding 228 can have a shape memory corresponding to the collapsed position 216 of the filter 214. Here, in operation, the braided scaffolding 228 having a normally collapsed shape memory urges the filter into the collapsed position absent application of a sufficient opposing force.

In another aspect, each wire of the plurality of wires 230 can be formed from a non-shape memory material, for example and without limitation, a cobalt chromium alloy, a stainless steel alloy, a molybdenum rhenium alloy, a plastic, and the like. In yet another aspect, some of the plurality of wires 230 can be formed from a shape memory material and the remainder of the plurality of wires can be formed from a non-shape memory material.

In another aspect, at least one of the plurality of wires 230 comprises a substantially round cross-section. In a further aspect, the round cross-section can range from about 60 to about 120 microns in diameter, more particularly, can be about 100 microns in diameter. In another aspect, at least one of the plurality of wires comprises a substantially rectangular cross-section. In a further aspect, the rectangular cross-section can have at least one of a height and a width of from about 60 to about 150 microns.

Figure 8A:
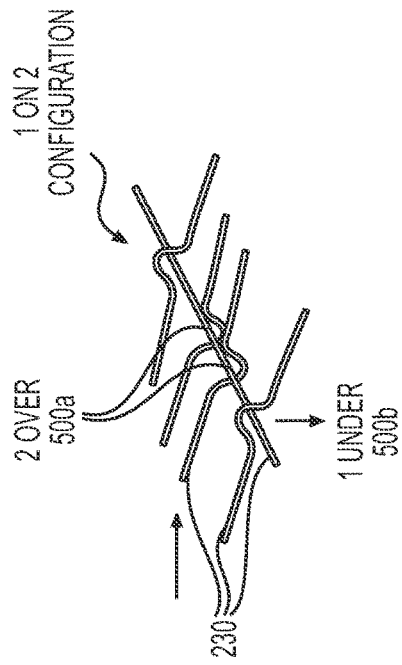
FIG. 8A provides a partial view of an example tubular braided scaffolding.
Figure 8B:
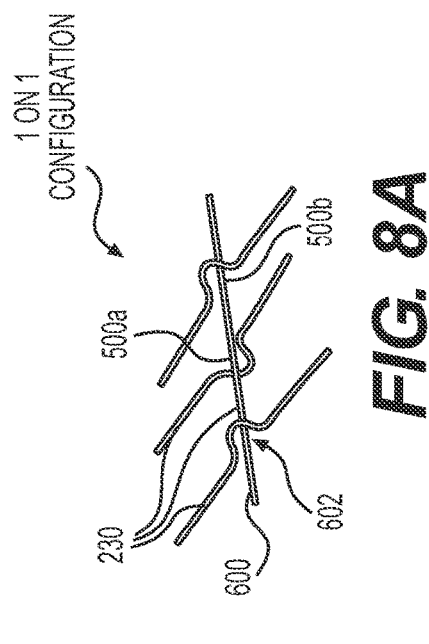
FIG. 8B provides a partial view of an example tubular braided scaffolding.

In yet another aspect illustrated in FIGS. 8A and 8B, the braided scaffolding 228 can be further characterized by the number of wire cross-overs 500a and 500b per inch along the length of each wire of the plurality of wires, hereinafter referred to as "picks per inch." It is contemplated that the braided scaffolding can have from about 6 to about 20 picks per inch, more preferably from about 7 to about 12 picks per inch, and, most preferably, about 9 picks per inch.

In yet another aspect, the braided scaffolding can be further characterized by the pattern of relative "over" or "under" placement of the wire cross-overs along the length of each of the plurality of wires. In one exemplary aspect illustrated in FIG. 8A, the braided scaffolding comprises a one-on-one configuration, meaning that the wire cross-overs along each of the plurality of wires alternate between one other wire crossing over 500a and one other wire crossing under 500b each wire. In another exemplary aspect illustrated in FIG. 8B, the braided scaffolding comprises a one-on-two configuration, meaning that the wire cross-overs along each of the plurality of wires has a pattern where two other wires cross over and one other wire crosses under each wire or vice-versa. FIG. 7 shows two different braided configurations with variations on the placement of the over versus under wires.

Figure 9:
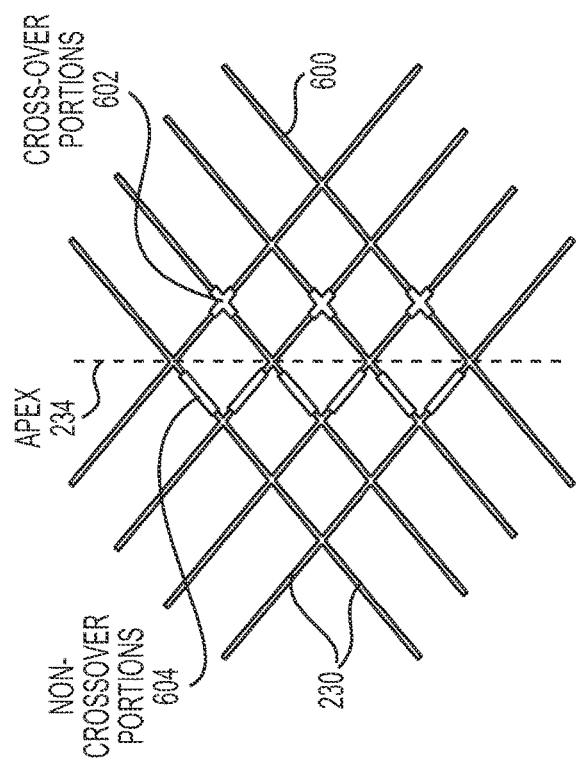
FIG. 9 provides a partial view of an example tubular braided scaffolding.

In another aspect illustrated in FIG. 9, each wire 600 of the plurality of wires 230 can further comprise at least one crossover portion 602 and at least one non-crossover portion 604. Here, a crossover portion 602 of a wire slidably contacts another wire of the plurality of wires 230 as the filter 214 moves between and about the collapsed position 216 to the deployed position 218. Correspondingly, a non-crossover portion 604 of a wire 600 does not contact any of the other wires of the plurality of wires 230 as the filter 214 moves between and about the collapsed position 216 and the deployed position 218. In a further aspect, the filter membrane 222 can be selectively attached to a plurality of the non-crossover portions 604 of the plurality of wires 230 of the braided scaffolding 228. In operation, selective attachment of the filter membrane 222 to a plurality of the non-crossover portions 604 of the plurality of wires 230 of the braided scaffolding 220 ensures the filter chassis 220 can open uniformly and to its full deployed position.

Referring to FIGS. 1-7 and also to FIG. 9, in another aspect, the filter chassis 220 has a central portion 232 having a maximum radial displacement, or apex 234 from the collapsed position 216 when the filter 214 is unconstrained and in the deployed position 218. It is contemplated that the filter membrane 222 can be selectively attached to the filter chassis 220 at a plurality of non-crossover portions 604 of the plurality of wires 230 of the braided scaffolding 228 located on or adjacent to the exterior of the apex 234 of the central portion 232 of the filter chassis 220.

Referring to FIGS. 1-7, another aspect, the filter membrane 222 can extend beyond the filter chassis 220 in a longitudinal direction relative to the longitudinal axis of the catheter such that a sac 236 is formed to retain embolic particles when the filter is in the collapsed position.

It is contemplated that the filter membrane 222 can comprise a polymer. In one aspect, the filter membrane 222 can be formed from polyurethane. In one aspect, the filter membrane 222 can be attached by thermal means, adhesive or by any other suitable attachment means known in the art.

Figure 10:
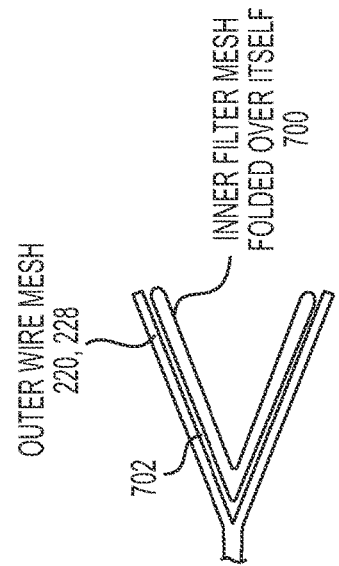
FIG. 10 provides a partial view of an example filter membrane.
Figure 11:
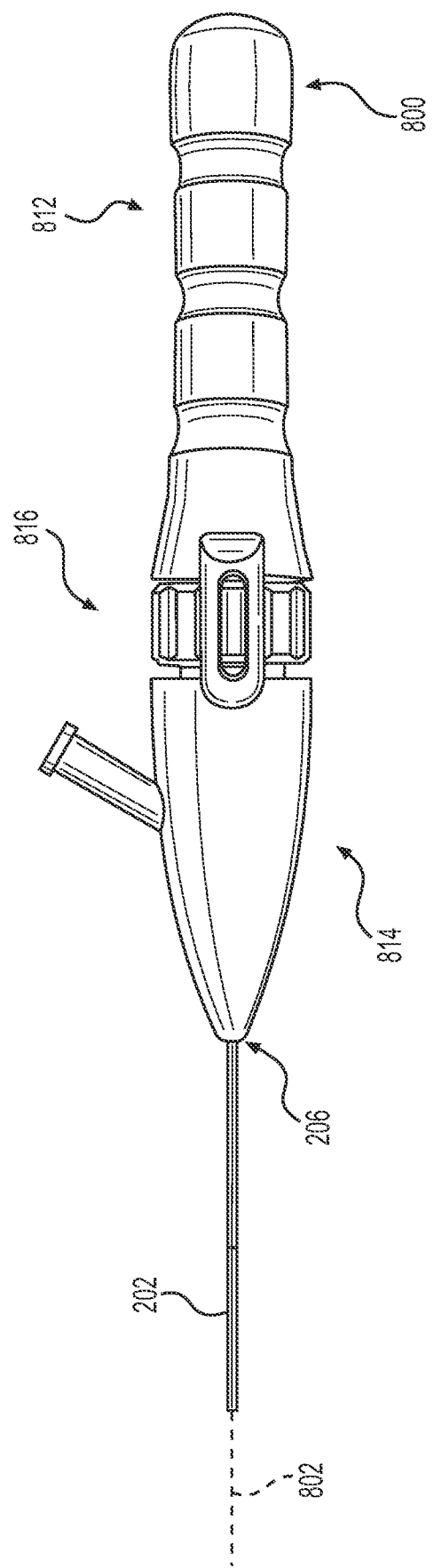
FIG. 11 provides a left side view of an example handle of a percutaneous transluminal device.
Figure 12:
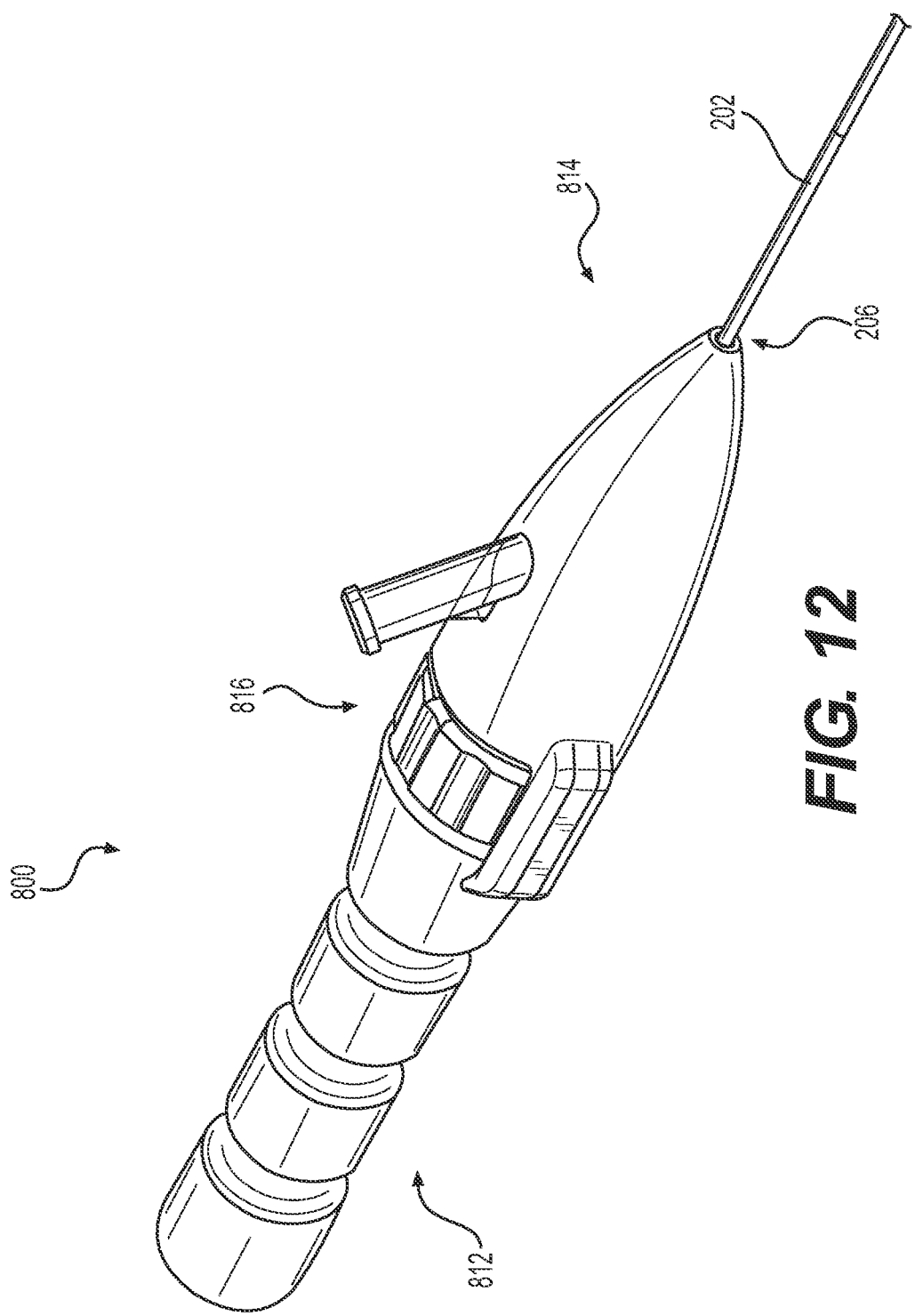
FIG. 12 provides a right side perspective view of the handle of FIG. 11.
Figure 13:
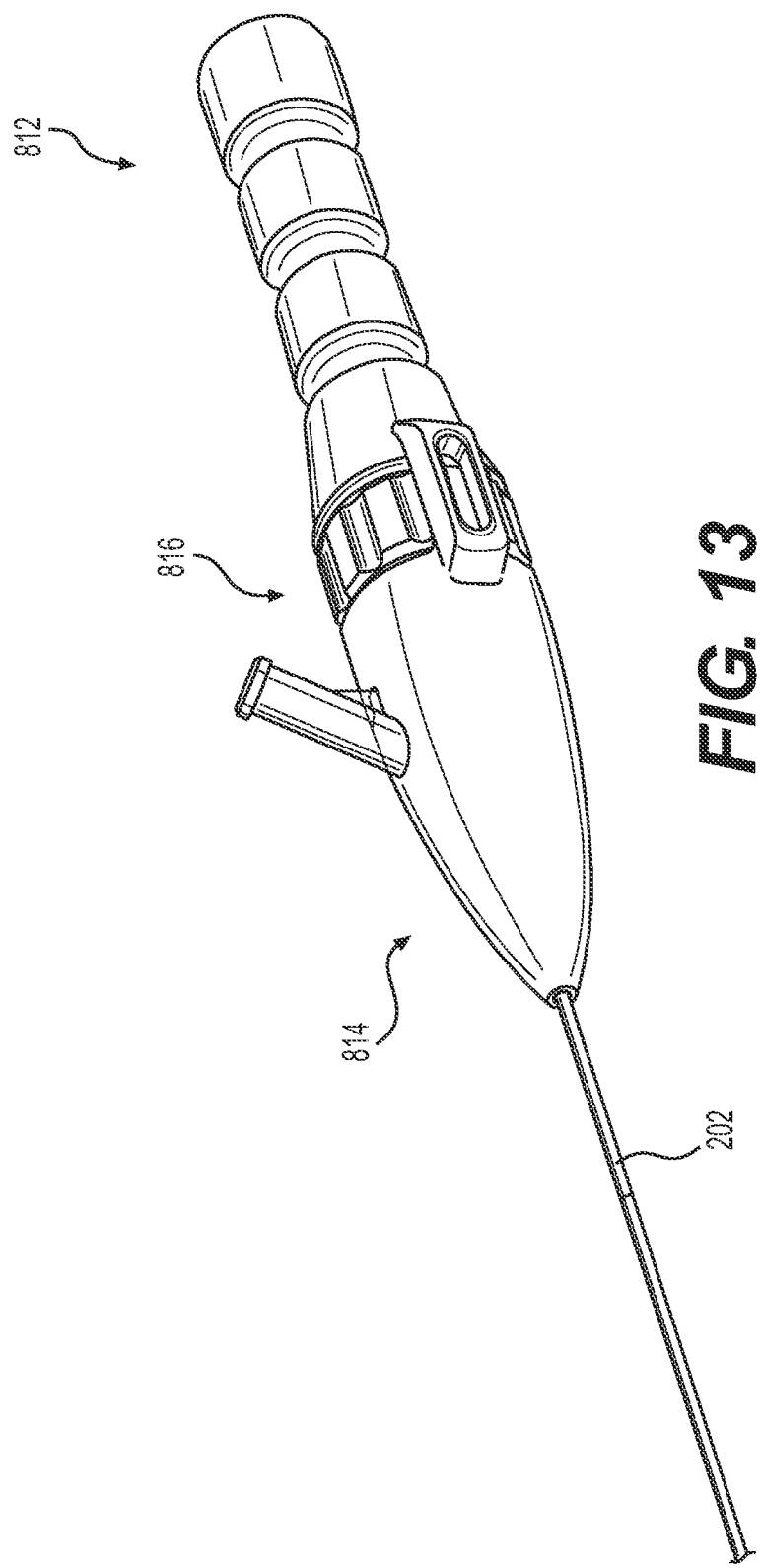
FIG. 13 provides a left side perspective view of the handle of FIG. 11.

As illustrated in FIG. 10, it is also contemplated that the filter membrane 222 can comprise a braided mesh 700 operably coupled to the filter chassis 220. In one aspect, the braided mesh 700 is disposed on an interior surface 702 of the filter chassis 220. In another aspect, the braided mesh 700 comprises about 64 wires. In another aspect, the braided mesh 700 comprises N wires and is folded over to form an apparent mesh having 2N wires. In one exemplary aspect where the braided mesh 700 comprises about 64 wires, the apparent braided mesh comprises about 128 wires. In another aspect, the braided mesh 700 comprises a shape memory material. In a further aspect, the shape memory material of the braided mesh 700 corresponds to the deployed position of the filter 214 and the braided scaffolding 228 comprises shape memory material having a shape memory corresponding to the collapsed position of the filter 214. It is contemplated that such a filter can be particularly useful in relatively large vessels such as, for example and without limitation, the aorta. It is also contemplated that such a filter can open to diameters of up to about 50 mm. In operation, the filter mesh 700 acts as a spring to aid in the selective expansion of the filter 214.

In another aspect, the filter membrane 222 comprises from about a 40 to about a 100 micron mesh, and more particularly from about a 40 to about a 60 micron mesh, and, most particularly, from about a 50 micron mesh. It is further contemplated that the filter membrane 222 can have a tolerance of about 10 microns.

It is further contemplated that at least one of the movable collar 224 and the fixed collar 226 can comprise a polymer. In a further aspect, the polymer can comprise polyimide. In an even further aspect, an interior surface of the movable collar 224 further comprises a coating having a lower coefficient of friction that the movable collar material and, even further, the coating can comprise, for example and without limitation, PTFE and the like.

In another aspect, that the distal portion 238 of the movable collar 224 can have a tapered portion that narrows toward the distal-most end of the movable collar 224.

In a further aspect, the movable collar 224 can be located distal to the fixed collar 226 relative to the longitudinal axis of the catheter 202.

In another aspect, the catheter 202 can further comprise a lumen 240 and a port 242 in communication with the lumen, the port comprising an aperture 211 in the outer side wall 210 of the catheter 202 located in between the fixed collar 226 and the movable collar 224, and the lumen extending from the proximal end portion 206 of the catheter to the port 242.

It is contemplated that the device 200 further comprises an actuator wire 246 having a proximal end 248 and a distal end 250, wherein at least a portion of the actuator wire extends through the lumen of the catheter 202, and wherein the distal end of the actuator wire exits the lumen of the catheter through the port and is coupled to the movable collar 224.

In one operational aspect, when the filter 214 is in the collapsed position 216, pulling on the proximal end 248 of the actuator wire 246 exerts a force on the movable collar 224 in a direction relative to the longitudinal axis 204 of the catheter 202 that moves the movable collar 224 toward the fixed collar 226 and wherein selective movement of the movable collar 224 towards the fixed collar 226 causes a central portion 232 of the filter chassis 220 to radially expand thereby selectively expanding the filter 214 towards the deployed position 218.

Figure 14:
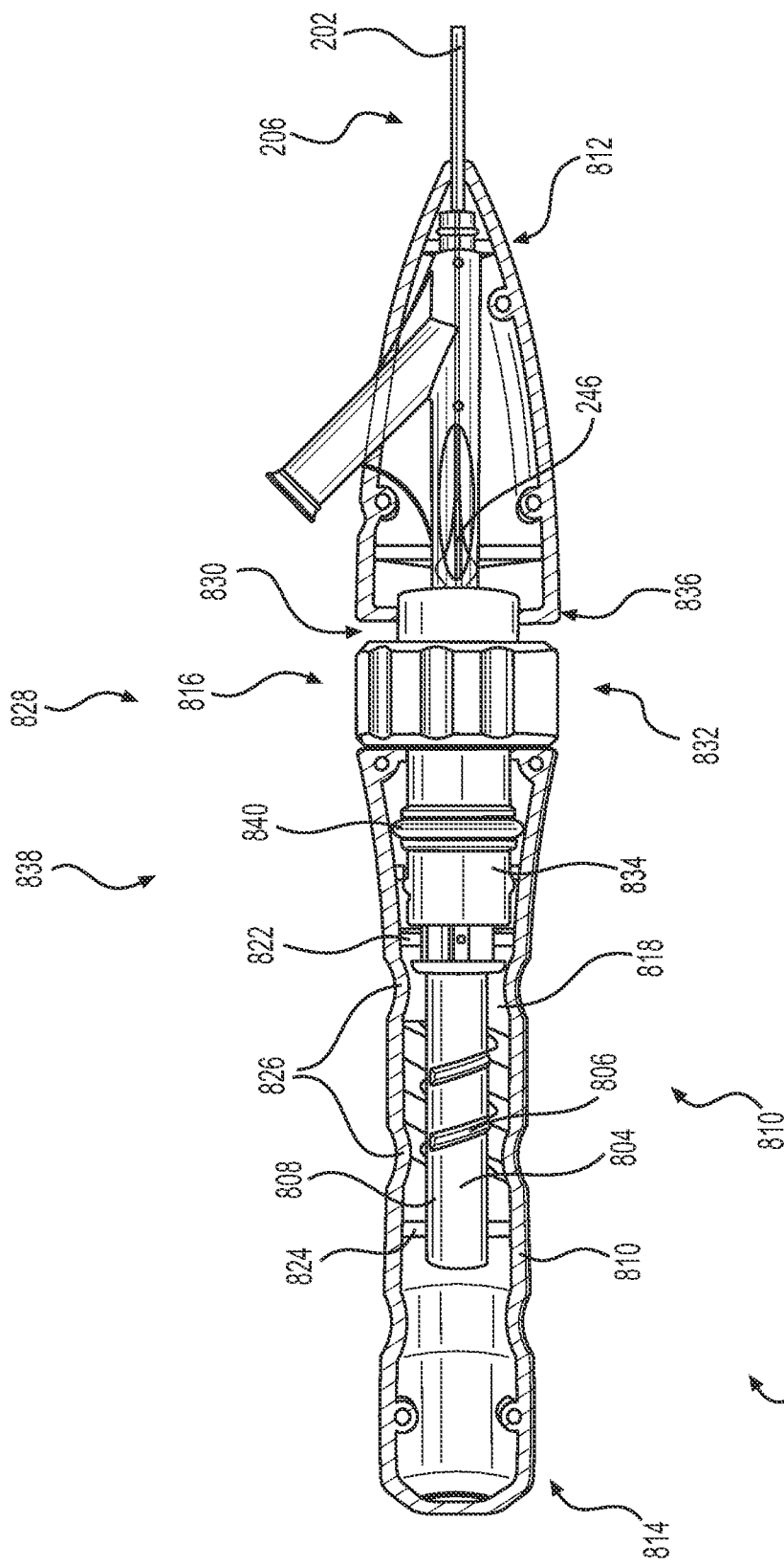
FIG. 14 provides a right side partial section view of the handle of FIG. 11.
Figure 15:
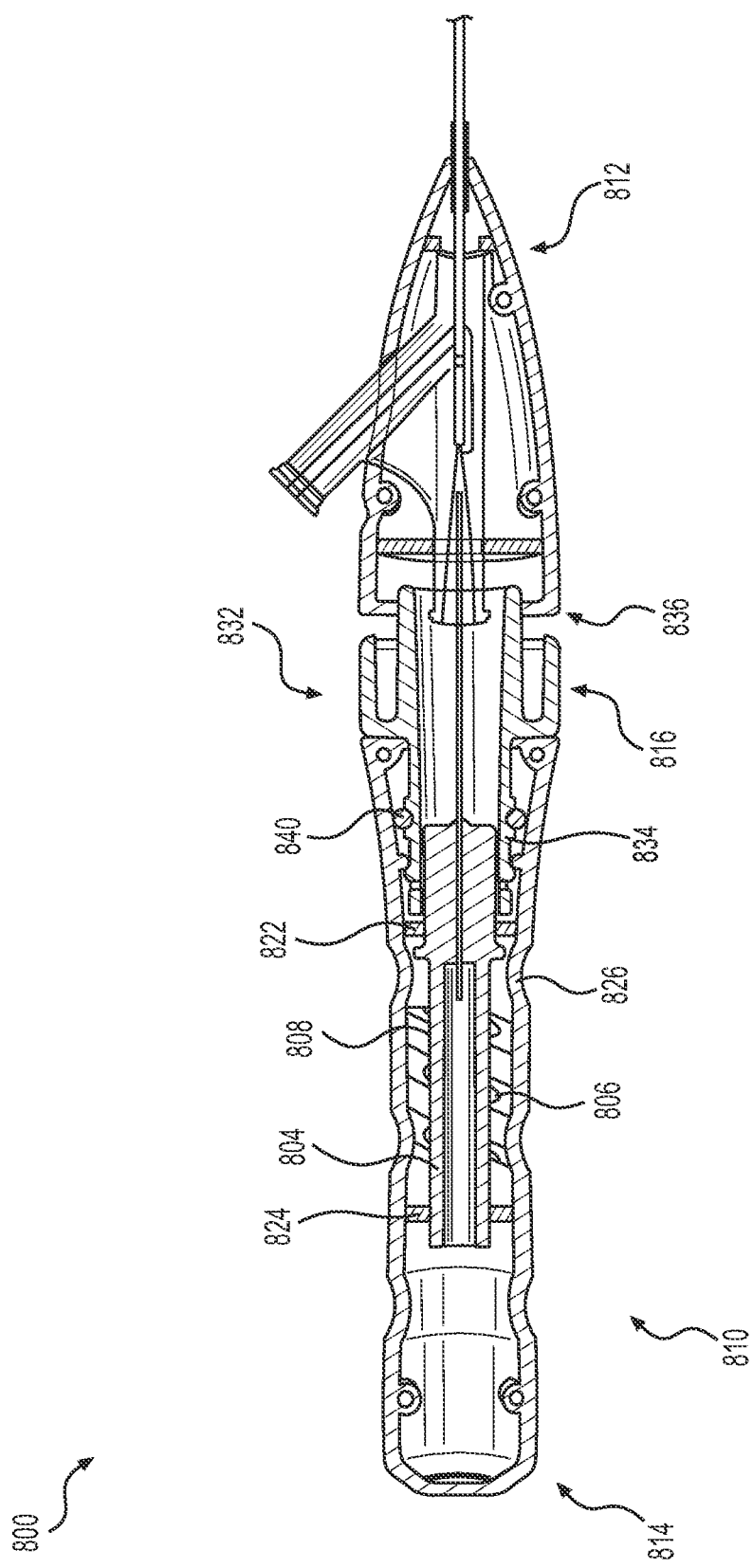
FIG. 15 provides a right side section view of the handle of FIG. 11.

In one aspect illustrated in FIGS. 11-15, the percutaneous transluminal device 200 comprises a handle 800 coupled to the proximal end of the proximal end portion 206 of the catheter 202 and operably coupled to the proximal end of the actuator wire 246. The handle has a longitudinal axis 802 that can be coextensive with the catheter longitudinal axis. As shown in FIGS. 14-15, the handle can further comprise a screw 804 having at least one thread 806 disposed on an exterior surface 808 thereof, wherein the screw 804 can be coupled to the actuator wire 246; a handle body 810 having a distal portion 812 and a proximal portion 814; and an actuator 816 coupled to the screw 804 and operably coupled to the handle body 810. It is contemplated that the actuator 816 can be configured to effect axial displacement of the screw 804, and, correspondingly, the actuator wire 246, relative to the handle longitudinal axis 802. In one aspect, the actuator 816 can be a knob and the knob can be rotatably coupled to the screw 804 along the longitudinal axis 802 of the handle 800.

In another aspect, each of the distal portion 812 and a proximal portion 814 of the handle body 810 can have respective inner surfaces that cooperate to define a respective chamber 818, 820. In one aspect, the proximal portion 814 of the handle 800 can further comprise a distal stop 822, a proximal stop 824, and a plurality of thread-receiving members 826 for engaging the at least one thread 806 of the screw disposed on an inner surface thereof and positioned between the distal and proximal stops 822, 824 relative to the handle longitudinal axis 802. It is contemplated that the distal stop 822 can limit distal axial movement of the screw 804 and the proximal stop 824 can limit proximal axial movement of the screw 804.

In another aspect, the knob can be positioned between the distal portion 812 and the proximal portion 814 of the handle body 810. Here, it is contemplated that the proximal portion 814 and the distal portion 812 of the handle 800 are spaced apart along the handle longitudinal axis 802 and the handle 800 further comprises at least one bridge portion 828 extending between and connected to the proximal portion 814 and the distal portion 812; wherein the proximal portion 814, distal portion 812 and the bridge portion 828 cooperate to define an opening for receiving at least a portion of the knob. In one aspect, the knob can have a hole extending through the rotational axis of the knob and can further comprise a distal portion 830, a central portion 832, and a proximal portion 834. In one aspect, the distal portion 812 of the handle 800 can have a proximal end 836 configured to receive at least a portion of the distal portion 830 of the knob. It is contemplated that the distal portion 830 of the knob can be positioned in at least one of slidable and rotatable engagement with the proximal end 836 of the distal portion 812 of the handle body 810. In another aspect, the proximal portion 814 of the handle body 810 has a distal end 838 configured to receive a proximal portion 834 of the knob. Here, it is contemplated that the proximal portion 834 of the knob can be positioned in at least one of slidable and rotatable engagement with the distal end 838 of the proximal portion 814 of the handle body 810.

In another aspect, the inner surface of the distal end 838 of the proximal portion 814 of the handle body 810 is inwardly tapered relative to the handle longitudinal axis 802 from the distal end 838 to the distal stop 822. It is further contemplated that the proximal portion 834 of the knob further comprises an O-ring 840 fixed to the outer surface thereof. Here, it is further contemplated that the knob can also be slidably disposed in the bridge portion 828. In operation, sliding the knob proximally relative to the handle longitudinal axis 802 can cause the O-ring 840 to engage the inwardly tapered inner surface of the proximal portion 814 which locks the rotational position of the knob. Conversely, sliding the knob distally relative to the handle longitudinal axis 802 unlocks the knob and allows further rotation. In operation, this O-ring locking mechanism can enable a physician to lock the filter 214 in any position about and between the collapsed position 216 and the deployed position 218. It is contemplated that such a feature, in combination with the disclosed filter 214, can be useful to adjust the expansion of the filter 214 towards the deployed position 218 and then secure the filter 214 in the selected position while the given intervention is effected.

In another aspect, each thread of the at least one thread 806 has a pitch 842. In one aspect, the pitch 842 of the at least one thread 806 can be selected to produce a desired axial movement of the screw 804 upon rotation. In a further aspect, the pitch 842 of the at least one thread can be selected to produce axial movement of the screw 804 along the handle longitudinal axis 802 equal to the circumferential movement of the knob.

In another aspect, the distal end of the distal portion 812 of the handle body 810 can further comprise an opening disposed therein for receiving the proximal ends of both the proximal portion of the catheter 202 and the actuator wire 246. In a further aspect, the distal portion 812 of the handle body 810 can further comprise a luer disposed therein and operably coupled to the distal portion 830 of the knob. In a further aspect, the luer comprises at least one port. Here, it is contemplated that at least the actuator wire 246 passes through the luer, through at least a portion of the hole disposed in the knob and is coupled to the actuator 816. In a further aspect, the actuator wire 246 can be coupled to the screw 804. In another aspect, the luer can comprise a second port and, in a further aspect, the second port can extend through a second opening formed in the distal portion 812 of the handle body 810.

In operation, rotating the screw 804 in either a clockwise or counterclockwise direction can move the actuator wire 246 back and forth along the catheter longitudinal axis 204. As described above, the actuator wire 246 is coupled to the movable collar 224 of the filter chassis 220. Accordingly, selective rotation of the screw 804 causes the movable collar 224 to be displaced relative to the fixed collar 226 along the catheter longitudinal axis 204. In a first rotational direction of the screw 804, the movable collar 224 is displaced toward the fixed collar 226, expanding the filter 214 towards the deployed position 218. In a second rotational direction of the screw 804, the movable collar 224 is displaced away from the fixed collar 226, moving the filter 214 towards the collapsed position 216. Accordingly, one skilled in the art will appreciate in light of the present disclosure that selectively rotating the screw 804 enables a physician to adjust the degree of expansion of the filter 214 to the target vessel. In one aspect, the screw 804 is actuated via a knob disposed in the bridge portion 828 of the handle 800 as described above. In a further aspect, a physician can secure the filter 214 in any position about and between the collapsed position 216 and the deployed position 218 by sliding the knob to engage the O-ring locking mechanism. It is contemplated that such a feature, in combination with the disclosed filter 214, can be useful to adjust the expansion of the filter 214 towards the deployed position 218 and then secure the filter 214 in the selected position while the given intervention is affected. As one skilled in the art will appreciate in light of the present disclosure, a physician (or any user) can selectively deploy the filter 214 and engage the O-ring locking mechanism and vice-versa with a single hand.

Figure 16:
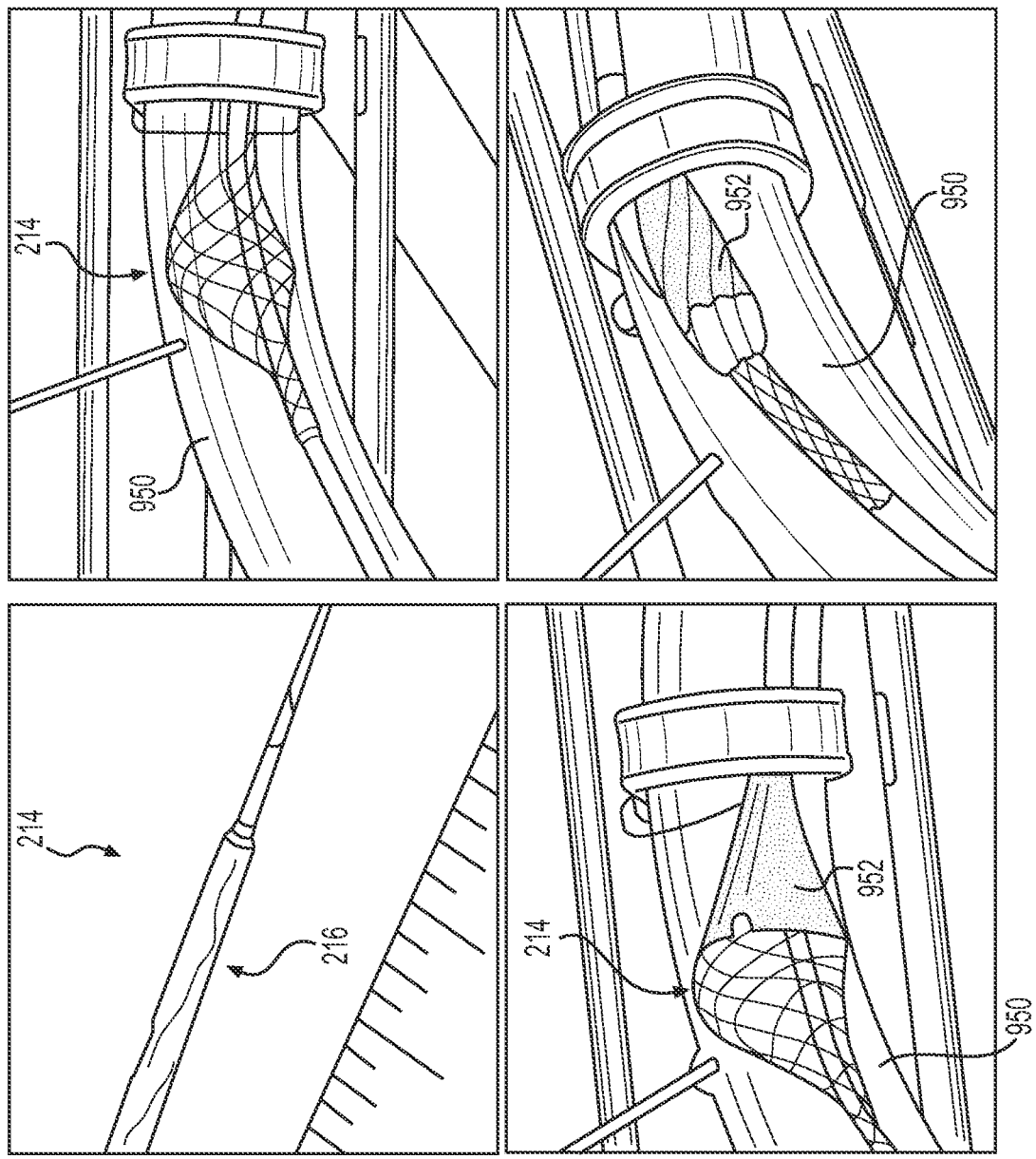
FIG. 16 provides from top left corner clockwise: the collapsed filter is shown in its initial state. The next figure shows the filter is deployed in an arterial model. The third figure shows the filter has captured particles. The last figure shows the filter is now collapsed trapping the particles within the filter membrane.

In another aspect illustrated in FIG. 16, the present disclosure describes a percutaneous transluminal device substantially as described above but having a filter 214 comprising a filter chassis 220 comprising a tubular braided scaffolding 228 having a distal end coupled to a movable collar that is slidably coupled to the catheter and having a proximal end that is coupled to a fixed collar that is spaced from the movable collar relative to the catheter longitudinal axis and immovably coupled to the catheter. FIG. 16 provides from top left corner clockwise: the filter 214 is shown in its initial collapsed state 216. The next figure shows the filter 214 is deployed in an arterial model 950. The third figure shows the filter has captured particles 952. The last figure shows the filter 214 is now collapsed trapping the particles 952 within the filter membrane 222.

In another aspect, the braided scaffolding can have a shape memory that urges the filter into the collapsed position. It is further contemplated that the braided scaffolding can have a central portion having a maximal radial displacement from the catheter longitudinal axis, or apex, that is greater than a target vessel radius when the filter is in the deployed position. In one aspect, when the filter is in the collapsed position, pulling on the proximal end of the actuator wire exerts a force on the movable collar in a direction relative to the longitudinal axis of the catheter that moves the movable collar toward the fixed collar. It is contemplated that selective movement of the movable collar towards the fixed collar causes the filter to selectively expand, thereby allowing the filter to conformably appose an inner wall of the target vessel. In the selectively expanded configuration, the filter captures substantially 100% of embolic particles having a particle size of at least 150 microns while remaining substantially patent during operation of the angioplasty treatment device and at least until the filter is collapsed for removal of the angioplasty device from the vessel. In another aspect, in the selectively expanded configuration, the shape of the conformably apposed filter and the pore size of the filter membrane cooperate to capture substantially 100% of embolic particles having a particle size of at least 150 microns while the filter remains substantially patent for up to about 5 minutes, more preferably, up to about 3 minutes, and, most preferably, up to about 1 minute. FIG. 17 is a table showing membrane particulate capture efficiency test results for the percutaneous transluminal device described in this disclosure.

Figure 18:
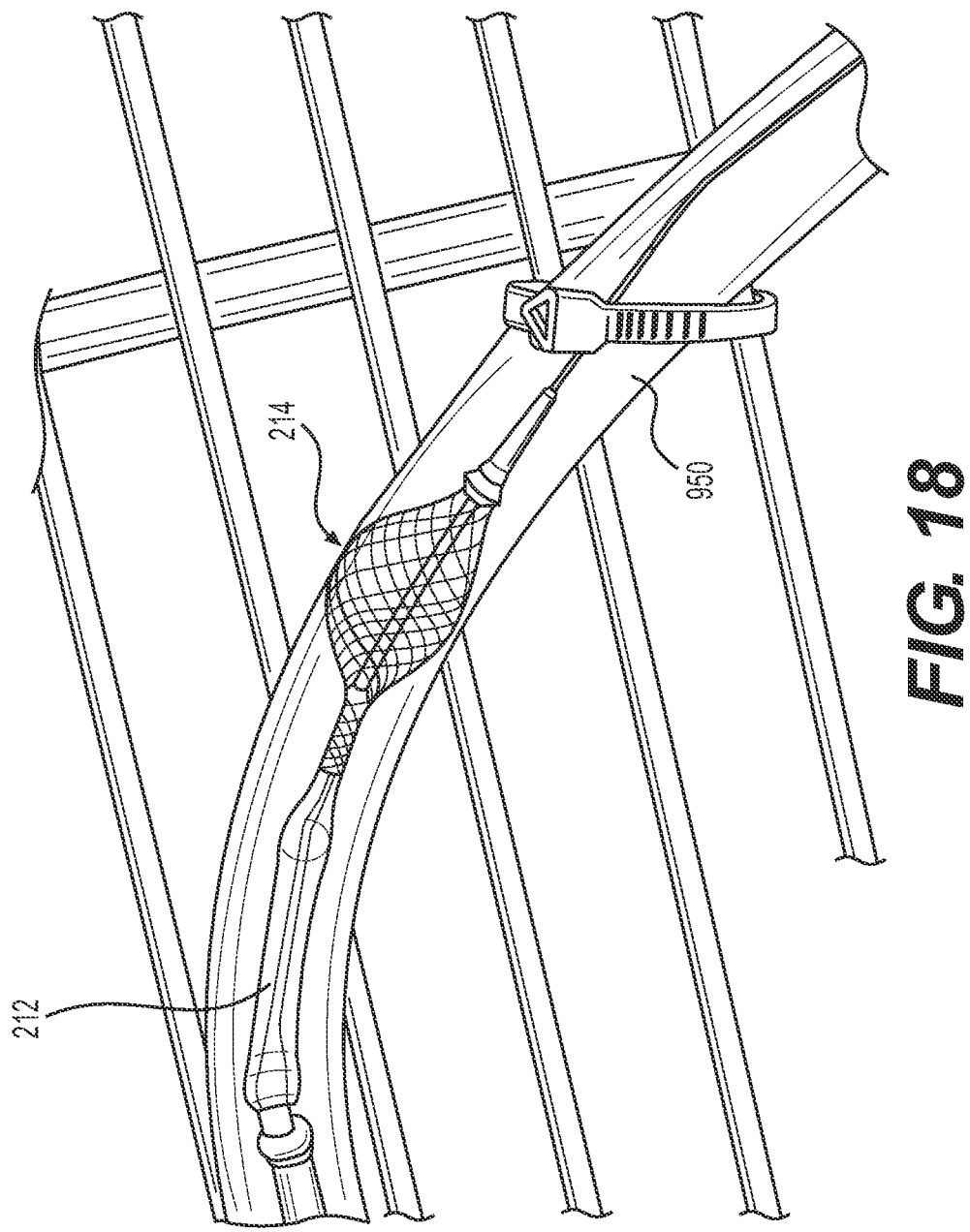
FIG. 18 provides the deployed filter inside an arterial model.
Figure 19:
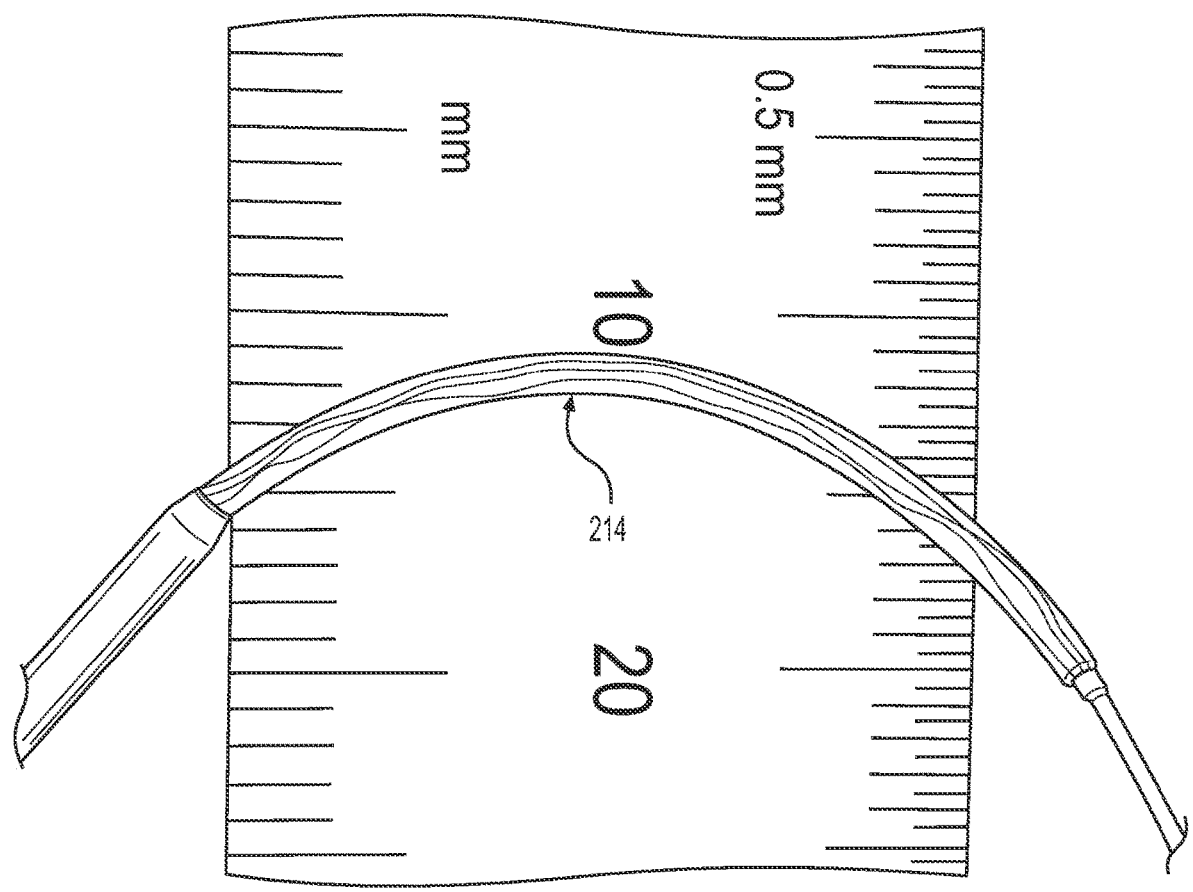
FIG. 19 provides the collapsed filter in a curvature.

FIG. 18 shows the filter 214 in its deployed state inside the model vessel 950. The filter conforms to the vessel walls and creates a tight seal so all particles are efficiently captured. FIG. 19 shows the filter 214 in a bend. It depicts the flexibility of the filter 214 to navigate through tight bends.

In yet another aspect illustrated in FIG. 20, the present disclosure describes a percutaneous transluminal device 900 comprising an elongated catheter 902 having a longitudinal axis 904, a proximal end portion 906, a distal end portion 908, and an outer side wall 910; an interventional device 912 operably coupled to at least the distal end portion of the catheter, and a filter 914 operably coupled to the distal end portion of the catheter, wherein the filter can be selectively collapsible and expandable about and between a collapsed position 216 and a deployed position 918. In this aspect, it is contemplated that the percutaneous transluminal device 900 can comprise any of the aspects described above and illustrated in FIGS. 1-19, unless otherwise noted herein. In one aspect, the elongated catheter is further configured to have a second lumen 920 disposed therein and adapted for slidably receiving at least a portion of a guidewire 922. It is further contemplated that the interventional device 912 comprises an atherectomy device. The atherectomy device can comprise a directional atherectomy device, a rotational atherectomy device or a combination thereof. In another aspect, the elongated catheter 912 further comprises a first elongate catheter 912 and a second elongate catheter 924 having a longitudinal axis 926 coextensive with that of the first catheter 912, a proximal end portion 928, a distal end portion 930, and a lumen 932 disposed therein for slidably receiving at least a portion of the first elongate catheter 912. It is contemplated that the interventional device 912 is disposed on the distal end portion 930 of the second catheter 924. In a further aspect, the interventional device 912 is located proximal to the filter with respect to the longitudinal axis 904 of the first catheter 902.

It is contemplated that the first elongate catheter 902 can comprise a polymer. In a further aspect, for example and without limitation, the polymer can comprise silicone, polyurethane, polyethylene, PTFE and the like. Alternatively, it is contemplated that the first elongate catheter 902 can comprise a metal. Here, it is contemplated that the metal catheter can be, for example and without limitation, a 0.014″, 0.018″, 0.035″ wire, having at least one and, preferably, two lumens disposed therein.

Accordingly, FIGS. 1-20, and the corresponding text, provide a number of different artificial turf configurations, as well as the devices, methods to form the different artificial turf configurations. In addition to the foregoing, implementations described herein can also be described in terms acts and steps in a method for accomplishing a particular result. For example, a method comprising providing a percutaneous transluminal device according to the present disclosure, inserting the distal portion of the device into a vessel such that the interventional device and the filter are located in a target location, deploying the integrated filter of the device, operating the interventional device; collapsing the integrated filter, and withdrawing the device from the body is described concurrently above with reference to the components and diagrams of FIGS. 1-20.

The present invention can thus be embodied in other specific forms without departing from its spirit or essential characteristics. The described aspects are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed:

1. A method of performing an interventional vascular procedure, the method comprising:
    advancing a catheter, an interventional device, and a filter into the vasculature of a subject, the filter comprising a movable collar encircling the catheter, the method further comprising;
    rotating a knob on an outside surface of a handle of the interventional device, the knob effecting rotation of a screw;
    rotating the screw in a first direction within the handle of the interventional device;
    axially translating the screw within the handle of the interventional device;
    axially moving an actuator wire within a lumen of the catheter;

pulling the movable collar with a distal end of the actuator wire;

deploying the filter at a position distal to the interventional device;

abutting a stop within the handle, thereby limiting axial movement of the screw and further deployment of the filter;

locking rotation of the knob by axially sliding the knob relative to the handle;

deploying the interventional device; and performing the interventional vascular procedure.

2. The method of claim 1, wherein axially sliding the knob causes an O-ring on the knob to engage a tapered inner surface of the handle.

3. The method of claim 1, wherein rotating the screw comprises engaging at least one thread of the screw with a thread receiving member within the proximal handle.

4. The method of claim 1, wherein a proximal end of the actuator wire is coupled to the screw, such that rotation of the screw effects axial movement of the actuator wire.

5. The method of claim 1, wherein pulling the movable collar further comprises sliding the movable collar axially along the catheter and toward a fixed collar of the filter, the fixed collar immovably coupled to the catheter.

6. The method of claim 5, further comprising longitudinally compressing a scaffolding of the filter between the movable collar and the fixed collar such that the scaffolding expands in diameter.

7. The method of claim 6, further comprising locking the filter when a diameter of the scaffolding matches a diameter of a target vessel.

8. The method of claim 1, further comprising conforming a scaffolding of the filter to a target vessel shape over a length of the target vessel.

9. The method of claim 8, wherein conforming a scaffolding to a target vessel shape further comprises conforming the scaffolding to a bend in the target vessel.

10. The method of claim 1, wherein a distal end of the actuator wire is coupled to the movable collar, and pulling the movable collar further comprises placing the actuator wire under tension.

11. The method of claim 10, further comprising releasing the tension in the actuator wire and collapsing the filter.

12. The method of claim 11, wherein releasing the tension in the actuator wire comprises rotating the screw in a second, opposite direction.

13. The method of claim 11, wherein a scaffolding of the filter has a shape memory bias toward a collapsed position, and collapsing the filter is a result of the shape memory bias.

14. The method of claim 1, further comprising moving the actuator wire through a port in a sidewall of the catheter.

15. The method of claim 1, further comprising capturing embolic particles within a filter membrane of the filter, wherein capturing embolic particles further comprises retaining embolic particles within a sac formed by the filter membrane upon the collapse of the filter, the sac positioned distal to the movable collar.

16. The method of claim 15, further comprising collapsing a filter scaffolding completely against a sidewall of the catheter while retaining the embolic particles within the sac positioned distal to the movable collar.

17. The method of claim 1, wherein the interventional vascular procedure comprises at least one of an angioplasty, a stenting, a thrombectomy, a valvuplasty, and an ablation.

18. The method of claim 1, wherein the filter is coupled to a filter membrane, the filter membrane having a mesh size of from 40 microns to 60 microns.

19. A method of performing an interventional vascular procedure, the method comprising:

advancing a catheter, an interventional device, and a filter into the vasculature of a subject, the filter comprising a movable collar encircling the catheter, the method further comprising;

rotating a knob on an outside surface of a handle of the interventional device, the knob effecting rotation of a screw;

rotating the screw in a first direction within the handle of the interventional device;

axially translating the screw within the handle of the interventional device;

axially moving an actuator wire within a lumen of the catheter;

pulling the movable collar with a distal end of the actuator wire;

deploying the filter at a position distal to the interventional device;

locking rotation of the knob by axially sliding the knob relative to the handle;

deploying the interventional device; and performing the interventional vascular procedure.

20. The method of claim 19, wherein axially sliding the knob causes an O-ring on the knob to engage a tapered inner surface of the handle.

* * * * *

UNITED STATES PATENT AND TRADEMARK OFFICE
CERTIFICATE OF CORRECTION

PATENT NO. : 11,844,679 B2
APPLICATION NO. : 17/512920
DATED : December 19, 2023
INVENTOR(S) : Ravish Sachar It is certified that error appears in the above-identified patent and that said Letters Patent is hereby corrected as shown below:

On the Title Page

Item (73) Assignee, Please change "Contego Medical, LLC" to --Contego Medical, Inc.--.

Signed and Sealed this
Twenty-first Day of May, 2024

Katherine Kelly Vidal
*Director of the United States Patent and Trademark Office*